(12) United States Patent
Hurmuzlu et al.

(10) Patent No.: US 8,408,049 B2
(45) Date of Patent: Apr. 2, 2013

(54) ULTRASOUND MULTIPHASE FRACTION METER AND METHOD FOR DETERMINING PHASE FRACTIONS IN A MULTIPHASE FLUID

(75) Inventors: Yildirim Hurmuzlu, Dallas, TX (US); Peter Antich, Dallas, TX (US); Ali Dogru, Dallas, TX (US); Edmond Richer, Dallas, TX (US); Billy Smith, Dallas, TX (US)

(73) Assignees: Multiphase Flow International, LLC, McKinney, TX (US); Board of Regents, The University of Texas System, Austin, TX (US); Saudi Arabian Oil Company, Dhahran (SA)

( * ) Notice: Subject to any disclaimer, the term of this patent is extended or adjusted under 35 U.S.C. 154(b) by 31 days.

(21) Appl. No.: 12/829,090

(22) Filed: Jul. 1, 2010

(65) Prior Publication Data
US 2010/0268487 A1    Oct. 21, 2010

Related U.S. Application Data

(62) Division of application No. 11/829,361, filed on Jul. 27, 2007, now Pat. No. 7,954,362.

(51) Int. Cl.
*G01N 37/00* (2006.01)
(52) U.S. Cl. .................................................. 73/61.44
(58) Field of Classification Search .................. 73/61.44
See application file for complete search history.

(56) References Cited

U.S. PATENT DOCUMENTS

| | | | |
|---|---|---|---|
| 4,080,837 A * | 3/1978 | Alexander et al. | 73/61.44 |
| 5,099,697 A * | 3/1992 | Agar | 73/861.04 |
| 6,209,388 B1 * | 4/2001 | Letton et al. | 73/61.79 |
| 6,601,458 B1 | 8/2003 | Gysling et al. | |
| 6,898,541 B2 | 5/2005 | Gysling et al. | |
| 2006/0053869 A1 | 3/2006 | Gysling et al. | |

* cited by examiner

*Primary Examiner* — Peter Macchiarolo
*Assistant Examiner* — Alex Devito
(74) *Attorney, Agent, or Firm* — Edwin S. Flores; Chainey P. Singleton; Chalker Flores, LLP

(57) ABSTRACT

An apparatus and method to determine fractions of various phases in a multiphase fluid. The apparatus includes main body including an interior configured receive a multiphase fluid and an exterior. The apparatus senses fluid pressure of multiphase fluid received in the interior and senses a fluid temperature of the multiphase fluid. The apparatus transmits an ultrasonic wave into the fluid and detects the transmitted wave to determine its velocity and attenuation. The apparatus may adjust the determined velocity and attenuation based on the temperature and pressure of the fluid to compensate for a difference between the sensed temperature and pressure and a standard temperature and pressure. The apparatus determines a gas fraction, water fraction, and a non-water fluid fraction of the multiphase fluid based on the sensed fluid pressure, the sensed fluid temperature, and the velocity and attenuation of the ultrasonic wave in the multiphase fluid.

23 Claims, 20 Drawing Sheets

Fig. 5A

ULTRASOUND MULTIPHASE FRACTION METER AND METHOD FOR DETERMINING PHASE FRACTIONS IN A MULTIPHASE FLUID

CROSS REFERENCES TO RELATED APPLICATIONS

This application is a divisional of U.S. application Ser. No. 11/829,361, filed Jul. 27, 2007, the entire content of which is incorporated herein by reference.

BACKGROUND

1. Field of Invention

This invention is directed to an ultrasound multiphase meter and method to detect and quantify the phase fractions and flow rates in a multiphase flow stream.

2. Description of the Related Art

Multiphase meters have attracted the attention of the oil production industry because of their accuracy and cost savings as opposed to analyzing discrete samples of multiphase fluid to determine fractions of oil, water, and gas. Development of accurate and compact multiphase metering devices that can be installed at well heads in remote onshore fields and unmanned offshore platforms continues to be a technological challenge. Data acquired by such devices may be used in reservoir management and production allocation inasmuch as the particular volumetric fractions of oil, water, and gas can be determined. Therefore this data is highly valuable. However, conventional devices have had difficulty in producing an accurate measurement of various properties of the monitored multiphase while withstanding the harsh environments in which such devices are typically installed.

Multiple array ultrasound devices that may acquire real time spatial data from volumetric specimens have been developed for medical applications. Advanced data and signal processing systems and display technologies have been developed for aerospace and the defense industries. These technologies are unsuitable to quantify phase fractions and flow rates of oil, gas, and water in a multiphase flow stream in an oil pipeline. In particular, the field conditions of the oil production environment are extremely harsh because of high pressure and temperatures and because of abrasive particles such as sand. Furthermore, the presence of gas bubbles in the flow streams as well as effects due to high temperature and pressure in the pipeline require specialized models to obtain accurate data collection and analysis.

SUMMARY OF THE INVENTION

According to one aspect of the invention, there is provided an apparatus configured to determine fractions of various phases in a multiphase fluid. The apparatus typically includes a main body including an interior configured to receive a multiphase fluid and an exterior, a pressure sensor configured to sense fluid pressure of multiphase fluid received in the interior, and a temperature sensor configured to sense a fluid temperature of the multiphase fluid. The apparatus also includes an ultrasonic transducer configured to transmit an ultrasonic wave in the multiphase fluid and an ultrasonic sensor configured to detect the ultrasonic wave transmitted by the ultrasonic transducer. A computer determines a gas fraction, water fraction, and a non-water fluid fraction of the multiphase fluid based on the sensed fluid pressure, the sensed fluid temperature, and at least one characteristic of the detected ultrasonic wave in the multiphase fluid. The at least one characteristic can be at least one of the velocity of the ultrasonic wave and the attenuation of the ultrasonic wave experienced as the wave travels from the ultrasonic transducer to the ultrasonic sensor.

According to another aspect of the invention, there is provided a method of determining fractions of various phases in a multiphase fluid. The method includes sensing a pressure of the multiphase fluid and sensing a temperature of the multiphase fluid. The method also includes transmitting an ultrasonic wave in the multiphase fluid, detecting the ultrasonic wave transmitted in the multiphase fluid, and determining a gas fraction, water fraction, and non-water fluid fraction of the multiphase fluid based on the sensed pressure, sensed temperature, and at least one characteristic of the detected ultrasonic wave. The at least one characteristic can be at least one of the velocity of the transmitted ultrasonic wave when it is detected and the attenuation of the ultrasonic wave when it is detected.

The apparatus can include a flow meter configured to measure an amount of fluid flowing in the apparatus. Based on this amount and the data determined regarding the water and gas fractions, the fraction of remaining fluid in the multiphase fluid can be determined via simple subtraction of the gas and water fractions from the total.

A multiphase meter according to one aspect of the invention includes a positive displacement volume flow meter, an ultrasonic phase fraction detector and a Doppler ultrasound detector. This multiphase meter includes two compact multi-transducer flow sensors designed to determine the water content and gas fraction in the oil mixture as well as to measure the liquid and gas phase velocities. Due to the harsh well head environment the ultrasound phase fraction detector is preferably made with appropriate thermal and mechanical strength.

According to another aspect of the invention, there is provided a computer readable medium containing program instructions for execution on a processor, which when executed by the processor, results in performance of certain steps including obtaining data relating to a pressure of a multiphase fluid and obtaining data relating to a temperature of the multiphase fluid. The steps also include receiving data regarding an ultrasonic wave transmitted in the multiphase fluid and determining a gas fraction, water fraction, and non-water fluid fraction of the multiphase fluid based on the data relating the pressure of the multiphase fluid, the data relating to the temperature of the multiphase fluid, and the data regarding the ultrasonic wave transmitted in the multiphase fluid.

According to another aspect of the invention, there is provided an apparatus configured to determine fractions of various phases in a multiphase fluid. The apparatus includes a main body including an interior configured receive a multiphase fluid and an exterior, a pressure sensor configured to sense fluid pressure of multiphase fluid received in the interior, and a temperature sensor configured to sense a fluid temperature of the multiphase fluid. The apparatus also includes an ultrasonic transducer configured to transmit an ultrasonic wave in the multiphase fluid and an ultrasonic sensor configured to detect the ultrasonic wave transmitted by the ultrasonic transducer. This aspect of the invention also provides means for determining a gas fraction, water fraction, and a non-water fluid fraction of the multiphase fluid based on the sensed fluid pressure, the sensed fluid temperature, and at least one characteristic of the detected ultrasonic wave in the multiphase fluid. The at least one characteristic can be at least one of the velocity of the ultrasonic wave and the attenuation of the ultrasonic wave experienced as the wave travels from the ultrasonic transducer to the ultrasonic sensor.

One application of the invention is to detect phase fractions of oil (non-water fluid), gas, and water in an oil pipeline, where attenuation of an ultrasound signal is used to determine the fraction, by volume, of gas bubbles in an oil/water/gas mixture, and velocity of a transmitted ultrasonic wave is used to determine the water fraction of the mixture.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, in which like reference numerals refer to identical or corresponding parts throughout the several views, and in which:

FIG. 5A is a detail of the graphical user interface of FIGS. 3A and 3B including peak detection and amplitude and velocity calculation according to an example embodiment of the invention;

DETAILED DESCRIPTION OF EXEMPLARY EMBODIMENTS

Figure 1A:
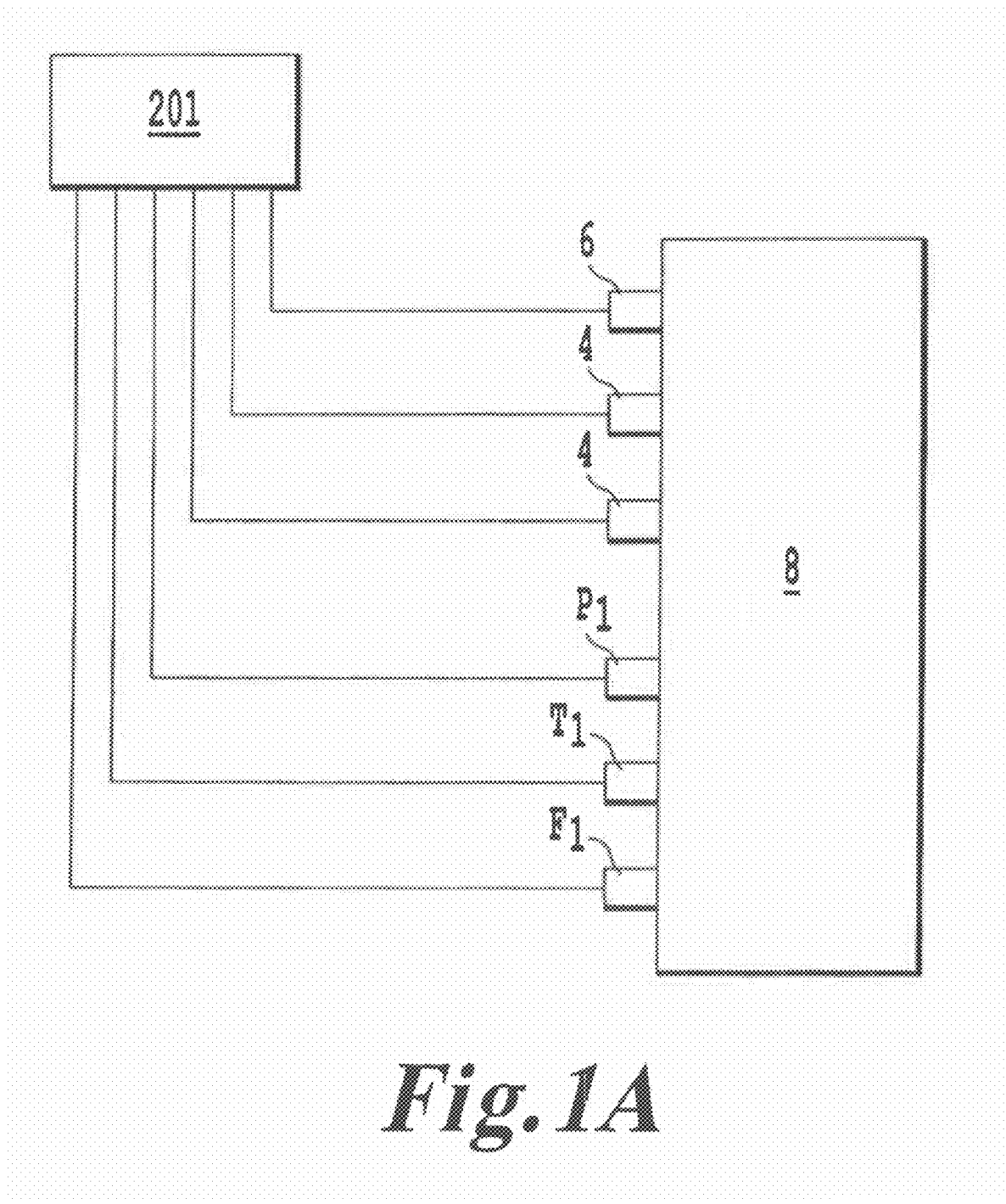
FIG. 1A is a block diagram schematically showing one aspect of the present invention.

FIG. 1A is a block diagram showing the functional relationship between a computer system 201 controlling and monitoring an Ultrasound Phase Fraction Detector 1 (UPFD 1) and the components within the UPFD 1. As shown in FIG. 1A, the computer system is connected to a sensor array 6, transducer(s) 4, pressure sensor P1, temperature sensor T1, and flow meter F1 (optional), all of which are connected to the main body 8 or configured to sense information from a main body 8. The main body 8 receives a multiphase fluid, and the computer system 201 receives information sent by the sensor array 6, pressure sensor P1, temperature sensor T1, and flow meter F1 (optional) relating to the multiphase fluid. The computer system 201 then analyzes the information to determine fraction of the multiphase fluid that is water, the fraction that is gas, and the fraction that is a non-water fluid, such as diesel fuel or oil.

Figure 1B:
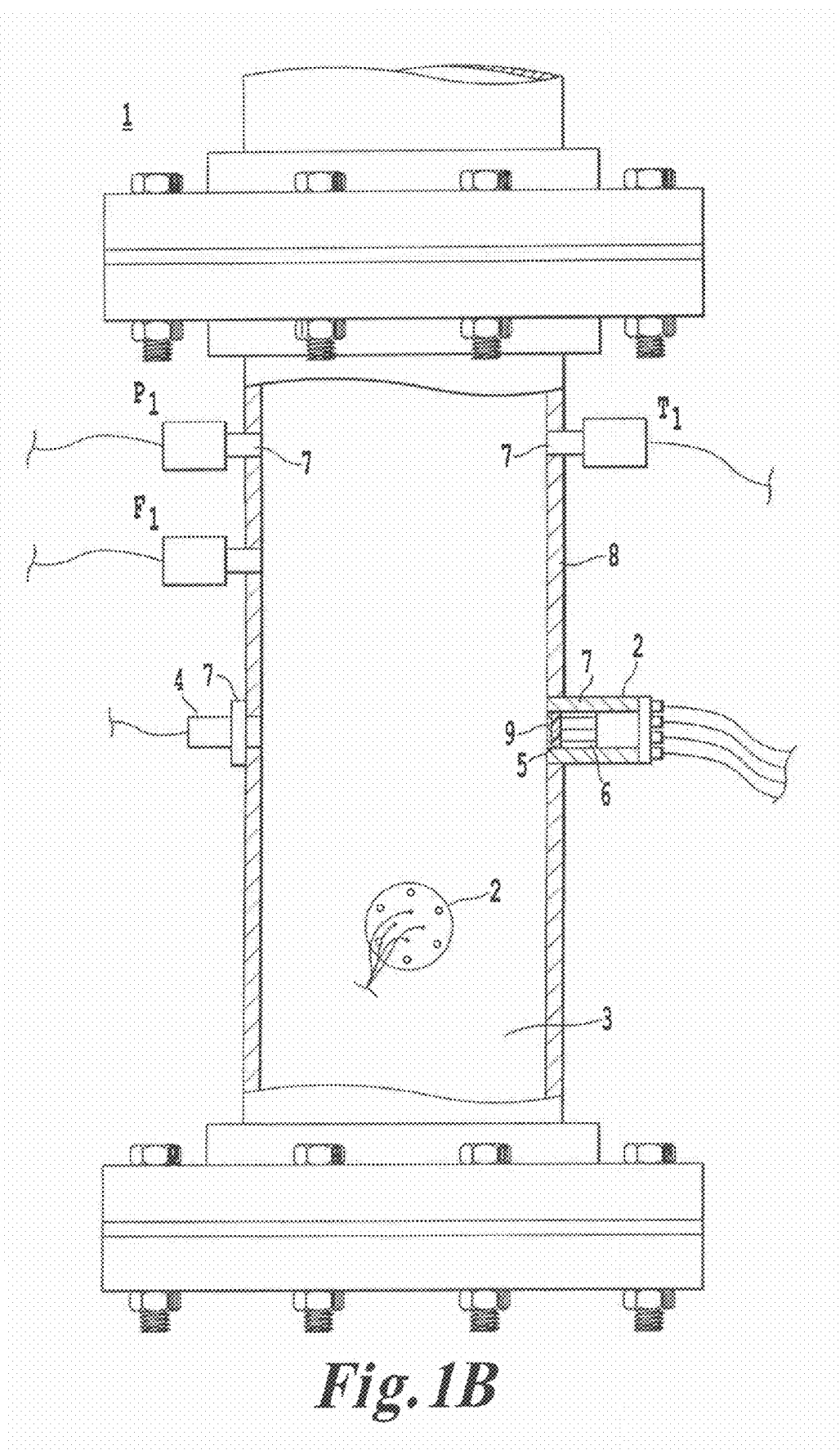
FIG. 1B is a schematic including cross sections of a pipeline with arrays, transmitters, pressure, and temperature sensors of an exemplary embodiment of the invention installed.

FIG. 1B shows one example of a UPFD 1 according to the present invention. In order to achieve the desired thermal and mechanical strength for industrial use, the body of the UPFD 1 of the embodiment shown in FIG. 1B is typically manufactured from materials that have similar mechanical and thermal characteristics to standard oil pipes. The main body 8 of the UPFD 1 may be formed from a segment of 316 stainless steel 4" pipe configured to withstand 300 psi and temperatures in excess of 500° F. Fittings 7 are attached, for example, by welding to the pipe in order to position and fix the ultrasound elements. The fittings are preferably made from 316 stainless steel, which allows welding to the pipe, or from brass, but other materials may be used. This construction enhances thermal and mechanical strength while providing good electrical conductivity for corresponding electrical grounding. Other materials such as 304 stainless steel, black pipe, or polymer pipes may be used, depending on the conditions and costs of a particular installation.

As further shown in FIG. 1B, sensitive elements are placed aligned with the inside wall of the pipe. In this configuration the sensitive elements are protected by a relatively thin metallic layer 9, a layer of TEFLON (FRP OR PTFE) 5, or other suitable material that does not excessively reduce the ability to capture the ultrasound signal. The thickness of the TEFLON layer may be, for example, 1.6 mm. Appropriate gaskets and other sealing compounds can also be used in the construction to facilitate sealing of the sensitive elements.

A plurality of piezoelectric (PZT) elements are embedded in the TEFLON layer as an ultrasonic sensor array 6. The sensor array 6 is typically mechanically fixed in a fitting 7, which may be made from stainless steel or brass. Use of these materials in the fitting 7 allows for an operating temperature range from −350° to 500° F. and pressures in excess of 300 psi. The fitting 7 can be a threaded connection or other such mechanical coupling. Alternatively, the sensor array 6 can be bonded to the wall of the main body 8 with an adhesive.

Ultrasound transducers 4 attached to the main body 8 are used as pulse transmitters. The ultrasound transducers 4 are preferably suitable for use in rugged industrial environments. The ultrasound transducers also preferably have an acoustic impedance matching most metals. If desired, an ultrasound pulse can be transmitted through a small thickness of the pipe, thus protecting the ultrasound sensor from the fluid inside the pipe. Transmitting through the wall of the pipe facilitates sealing. The ultrasound transducer 4 may be one such as those available from VALPEYFISHER, for example, model no. CS0.508HP-TC, which have a 1" active element with a 500 KHz frequency.

One example of the invention uses two pairs of transmitter and receiver arrays, one pair orthogonal to the other, so that the signal spans the entire cross sectional area of the pipe. This arrangement can also be used for flow velocity measurement by cross correlation of the signals.

As will be discussed, pressure and temperature are important parameters in determining the phase fractions and flow rates of oil, gas, and water in a multiphase flow stream. The propagation velocity of an ultrasound pulse depends on the temperature and pressure of the oil-water mixture 3 in which the pulse travels. Thus, UPFD 1 is provided with a pressure sensor P1 and temperature sensor T1 in order to allow these properties to be taken into account in the determination of the phase fractions.

A STELLAR TECHNOLOGY INC. pressure sensor model no. GT1800-500G-000 with the following characteristics was found suitable as a pressure sensor P1 in the above installation.

| | |
|---|---|
| Standard pressure range: | 0-500 PSIg |
| Proof pressure: | 750 PSIg |
| Burst pressure: | 1000 PSIg |
| Operating media: | fluids and gases compatible with 17-4PH stainless steel |
| Resolution: | infinite (analog) |
| Compensated temp. range: | +30° F. to +130° F. |
| Operating temp. range: | −40° F. to +185° F. |
| Enclosure: | Body and pressure cavity of stainless steel, environmentally sealed |

As a temperature sensor T1, a series T750-250 temperature sensor, also produced by STELLAR TECHNOLOGY INC., with the following characteristics was found suitable.

| | |
|---|---|
| Operating temp. range: | −65° F. to +250° F. |
| Burst pressure: | 30,000 PSI minimum |
| Operating media: | fluids and gases compatible with 17-4PH stainless steel |
| Resolution: | infinite (analog) |
| Enclosure: | Body and pressure cavity of stainless steel, hermetically sealed |

A flow meter F1 shown on the left side of the main body 8 in FIG. 1B is typically provided to determine the total flow through the UPFD 1. Various types of flow meters may be used for this application. For example, paddle wheel flow meters may be used.

A controller or computer system 201 (shown in FIG. 2) uses a combination of data from the pressure sensor P1, flow meter F1, temperature sensor, T1, and sensor array 6 to detect and quantify phase fractions and flow rates of oil, gas, and water in a multiphase flow stream inside the main body 8.

Figure 2:
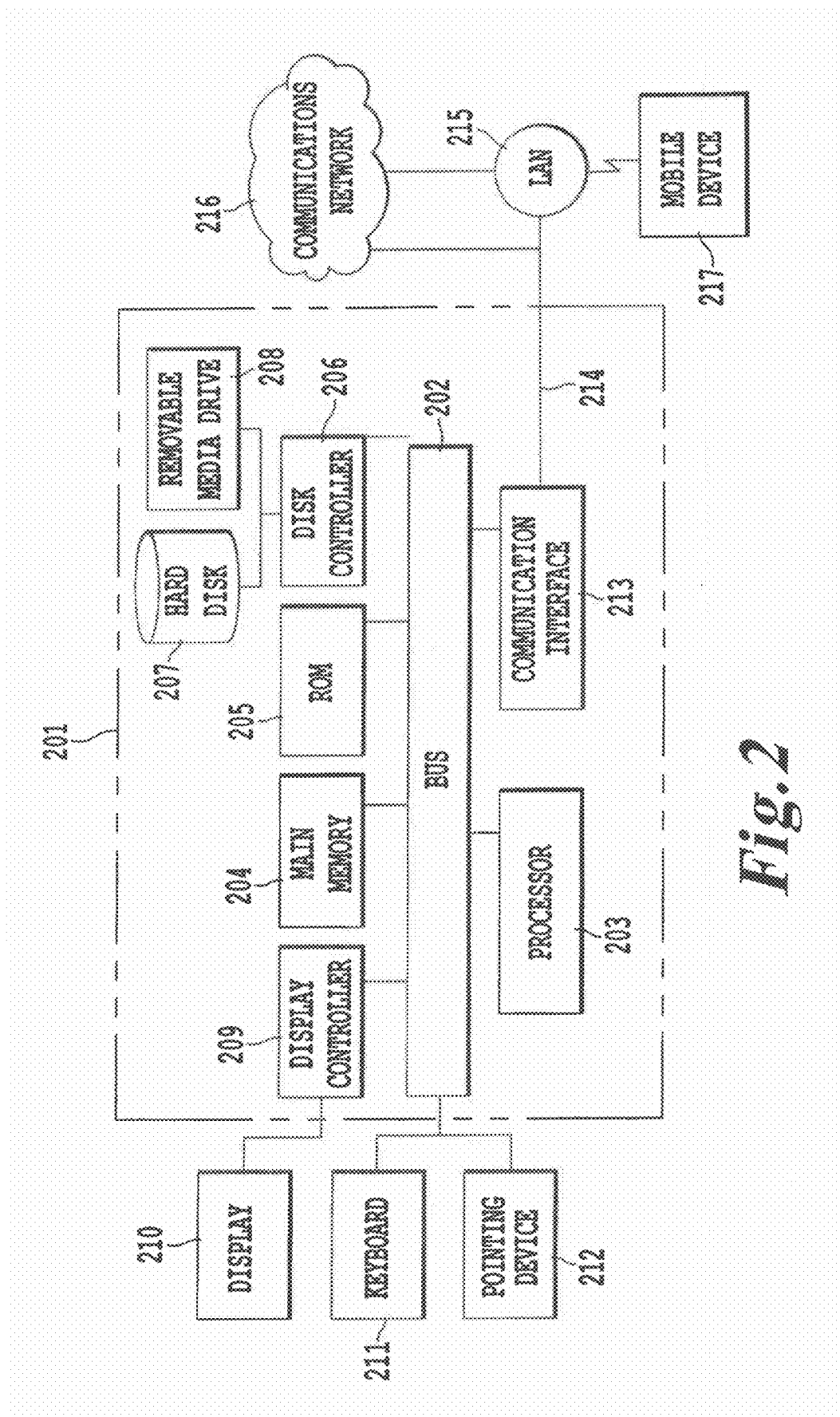
FIG. 2 is a block diagram of a computer system and its main components.

FIG. 2 illustrates a typical computer system 201 upon which an embodiment of the present invention may be implemented. All or merely selected processing components of the embodiments discussed herein may by implemented. The computer system 201 includes a bus 202 and a processor 203. The computer system 201 also includes a main memory 204, such as a random access memory (RAM). The computer system 201 further includes a read only memory (ROM) 205 or other static storage device (e.g., programmable ROM (PROM), erasable PROM (EPROM), and electrically erasable PROM (EEPROM)) coupled to the bus 202.

The computer system 201 also includes a disk controller 206 to control one or more storage devices such as a magnetic hard disk 207 and a removable media drive 208 (e.g., floppy disk drive).

The computer system 201 may also include a display controller 209 coupled to the bus 202 to control a display 210 for displaying information to a computer user. The computer system may include input devices, such as a keyboard 211 and a pointing device 231.

The computer system 201 performs a portion or all of the processing steps of the invention by virtue of the processor 203 executing one or more sequences of one or more instructions contained in a memory, such as the main memory 204. Such instructions may be read into the main memory 204 from another computer readable medium, such as a hard disk 207 or a removable media drive 208.

Software is stored on any one or on a combination of computer readable media to control the computer system 201, to drive a device or devices for implementing the invention, and for enabling the computer system 201 to interact with a human user.

The term "computer readable medium" as used herein refers to any medium that participates in providing instructions to the processor 203 for execution. A computer readable medium may take many forms, including but not limited to, non-volatile media, volatile media, and transmission media. Non-volatile media includes, for example, optical, magnetic disks, and magneto-optical disks, such as the hard disk 207 or the removable media drive 208. Volatile media includes dynamic memory, such as the main memory 204. Transmission media includes coaxial cables, copper wire and fiber optics, including the wires that make up the bus 202.

Various forms of computer readable media may be involved in carrying out one or more sequences of one or more instructions to processor 203 for execution. For example, the instructions may initially be carried on a magnetic disk of a remote computer.

The computer system 201 may also include a communication interface 213 coupled to the bus 202. The communication interface 213 provides a two-way data communication coupling to a network link 214 that is connected to, for example, a local area network (LAN) 215, or to another communications network 216 such as the Internet. Wireless links may also be implemented for such connection. The communication interface 213 sends and receives electrical, electromagnetic or optical signals that carry digital data streams representing various types of information.

The network link 214 typically provides data communication through one or more networks to other data devices. For example, the network link 214 may provide a connection to another computer through a local network 215 (e.g., a LAN) or through equipment operated by a service provider, which provides communication services through a communications network 216. The local network 214 and the communications network 216 use, for example, electrical, electromagnetic, or optical signals that carry digital data streams, and the associated physical layer. The computer system 201 can transmit and receive data, including program code, through the network(s) 215 and 216, the network link 214 and the communication interface 213. Moreover, the network link 214 may provide a connection through a LAN 215 to a mobile device 217 such as a personal digital assistant (PDA) laptop computer, or cellular telephone.

The functionality of the UPFD 1 shown in FIGS. 1A and 1B may be completely automated. A signal received from the sensor array 6 is monitored and parameters of a pulse applied to the ultrasound transducers 4 are adjusted accordingly.

Figure 3A:
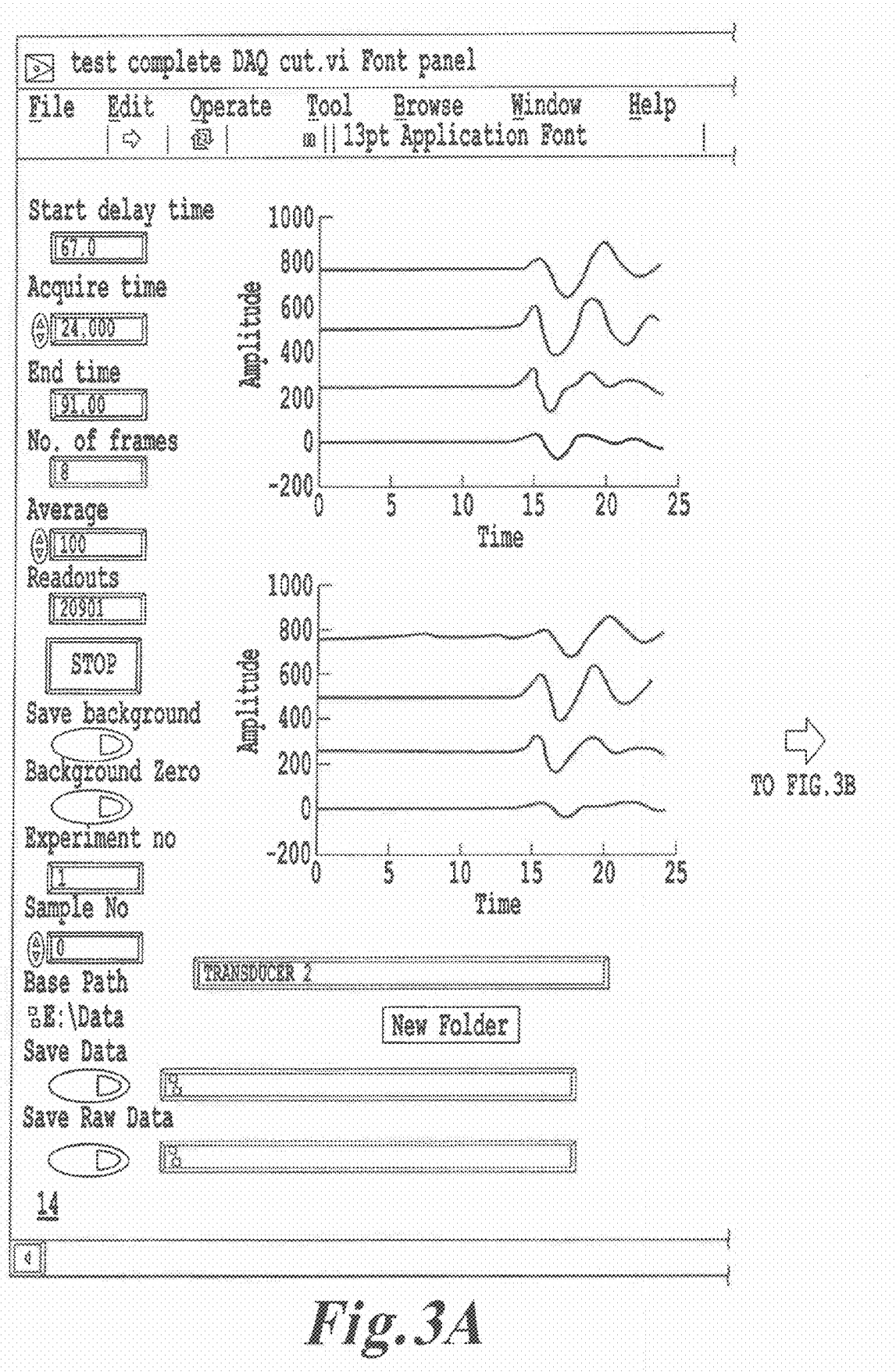
FIGS. 3A and 3B are a graphical user interface for data analysis including a user interface for data analysis according to an example embodiment of the invention.
Figure 3B:
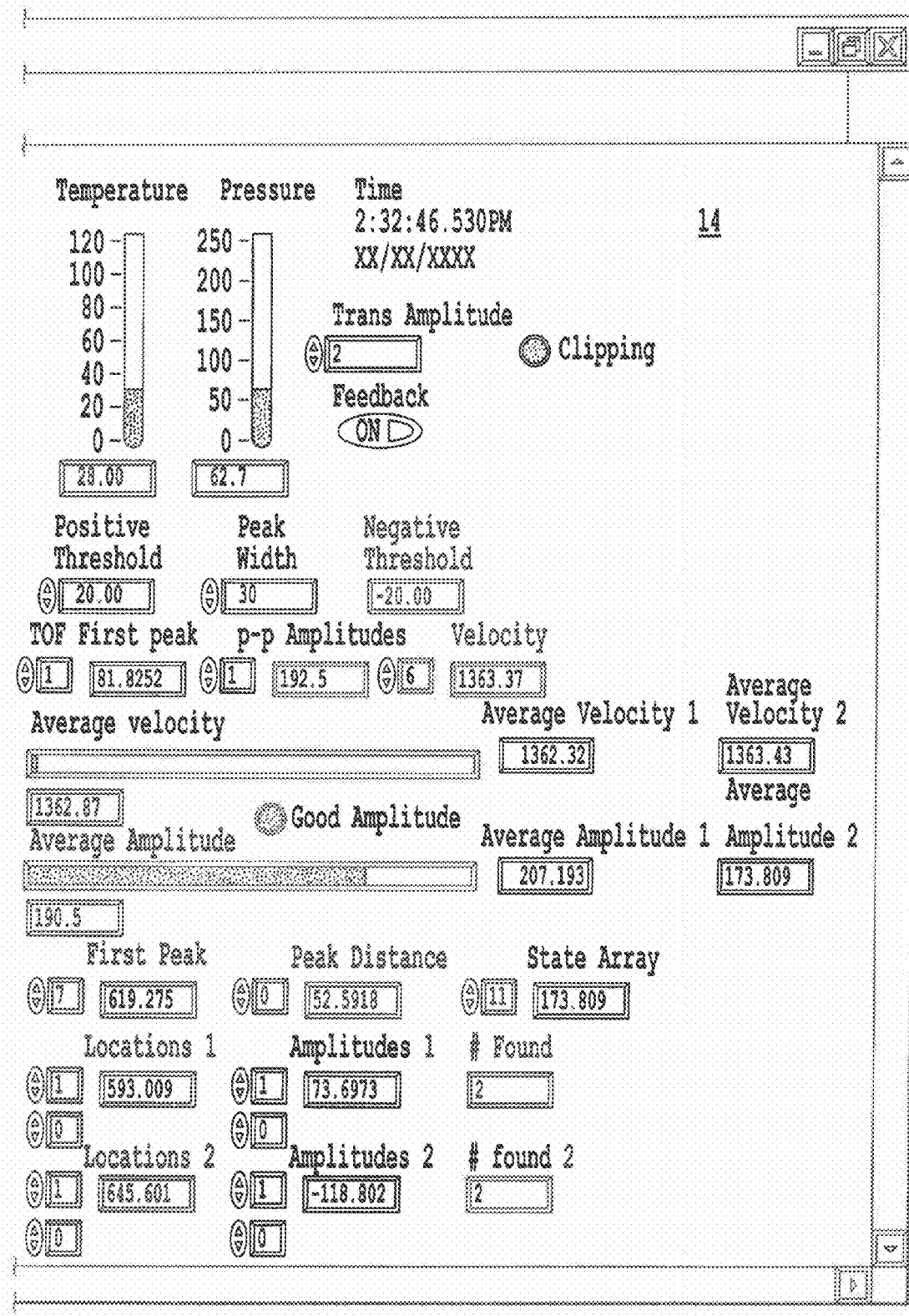
Figure 4A:
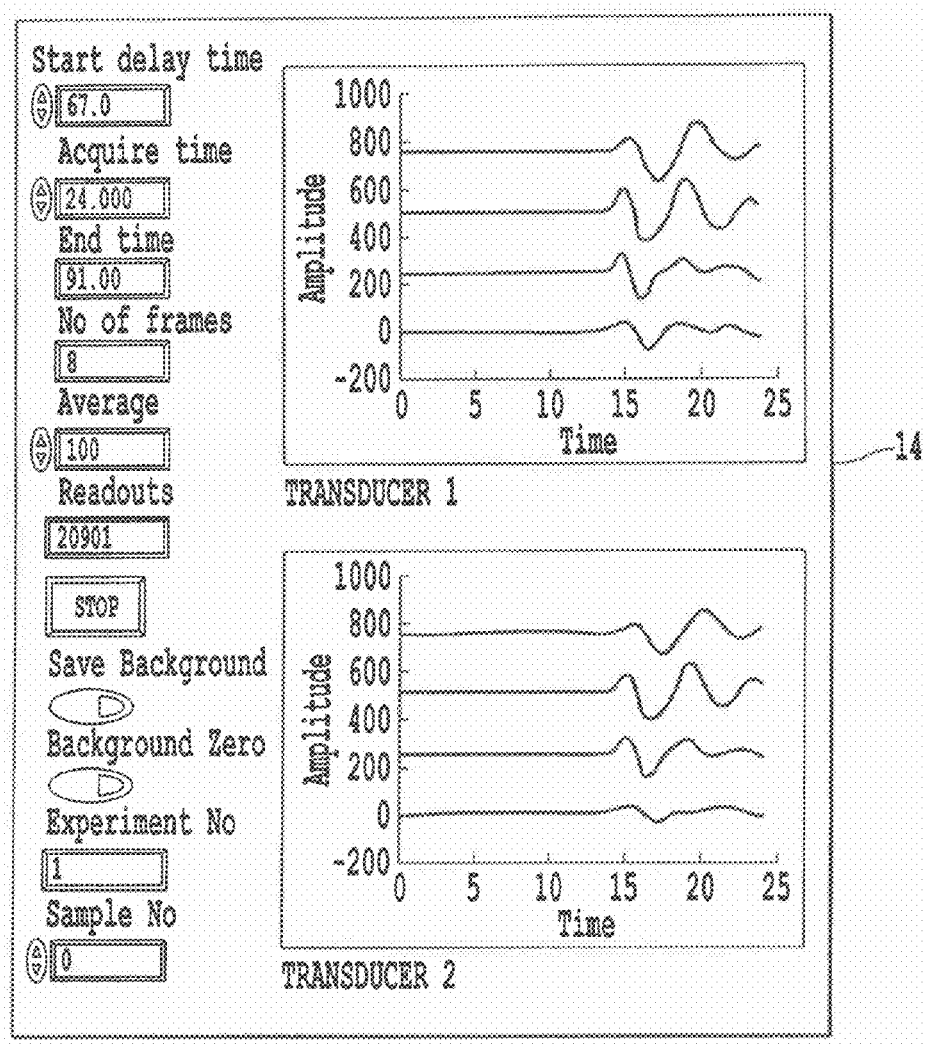
FIG. 4A is a detail of the graphical user interface of FIGS. 3A and 3B including data acquisition parameters and signal generation and monitoring according to an example embodiment of the invention.

A first set of parameters that can be adjusted are: delay time from the application of the pulse at the transmitter, acquire time, and the number of data sets to be averaged for noise suppression purposes. Also, the user may monitor the signal received at each ultrasound array channel in real time. Systematic background noise can be monitored and automatically subtracted from the analyzed waveform. FIGS. 3A, 3B, and 4A show typical displays of a user interface 14 displaying the amplitude vs. time, acquire time, and start delay time for one set of parameters.

Figure 4B:
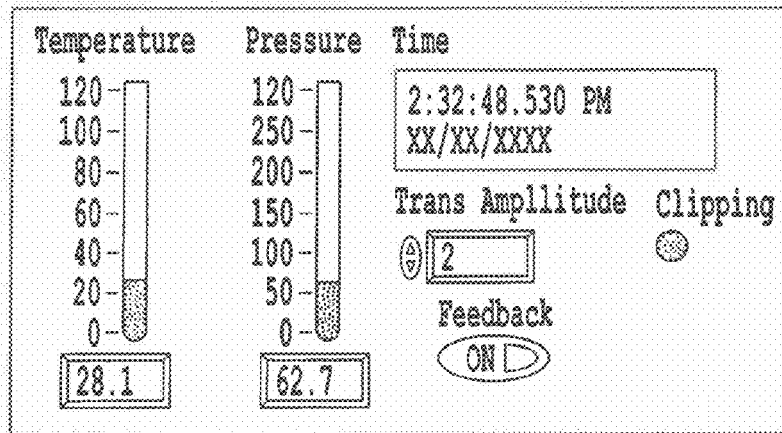
FIG. 4B is a detail of the graphical user interface of FIGS. 3A and 3B including temperature pressure, time and transmitter amplitude monitoring and adjustment according to an example embodiment of the invention.

Temperature and pressure measurements from the area around the transducers 4 are digitized and are monitored in real time as shown in the user interface 14 depicted in FIG. 4B. Also, the current time and the voltage applied to the ultrasound transmitters are recorded. A transmitter voltage can be adjusted by the operator (mostly for setup and maintenance) or, when the feedback button is activated, directly by the system. When large amounts of gas bubbles are present inside a volume monitored by the system, the attenuation of the transmitted signal is large, thus requiring a large pulse voltage at the transmitters. When only a small fraction of gas bubbles is present, the amplitude of the pulse applied to the ultrasound transducers 4 is preferably reduced in order to prevent clipping (truncation of the top part of the wave of the signal). This increase and decrease of the pulse amplitude, when done automatically, effectively increases the dynamic range of the flowmeter without operator intervention. Also, a mathematical model, discussed hereafter, to account for high pressure and temperature effect is typically incorporated in the system.

Data received by the pressure sensor P1, temperature sensor T1, and flow meter F1 is automatically analyzed and the results are stored on, for example, the computer hard drive at programmable intervals of time. These results can then be retrieved from a remote location by a simple network connection. The arrival of the ultrasound pulse is detected at each element of the sensor array 6 (shown in FIGS. 1A and 1B) and then the positive and the negative peaks in the waveform are detected. The time lapse between the positive and the negative peaks is then calculated, and if the time lapse is in the acceptable range (determined by the frequency of the pulse) the pulse amplitude and the time of flight are calculated.

A "Good Amplitude" test is performed by checking for signal clipping and for time differential between the positive and the negative peaks. No clipping means that there are no flat hysteresis portions on the top and bottom portions of the signal where it is maximum or minimum. The time differential means that the minimum and maximum are measured during the same cycle.

If a "Good Amplitude" test is made, and if the signal was not clipped, see "Clipping" indicator in FIG. 4B, a state vector is formed and saved. The state vector includes the current time, delay acquisition time, the acquisition time, number of waveforms averaged, pressure, temperature, transmitter amplitude, the two transducer average velocities, total average velocity, the two transducer amplitudes, and total average amplitude.

Figure 5A:
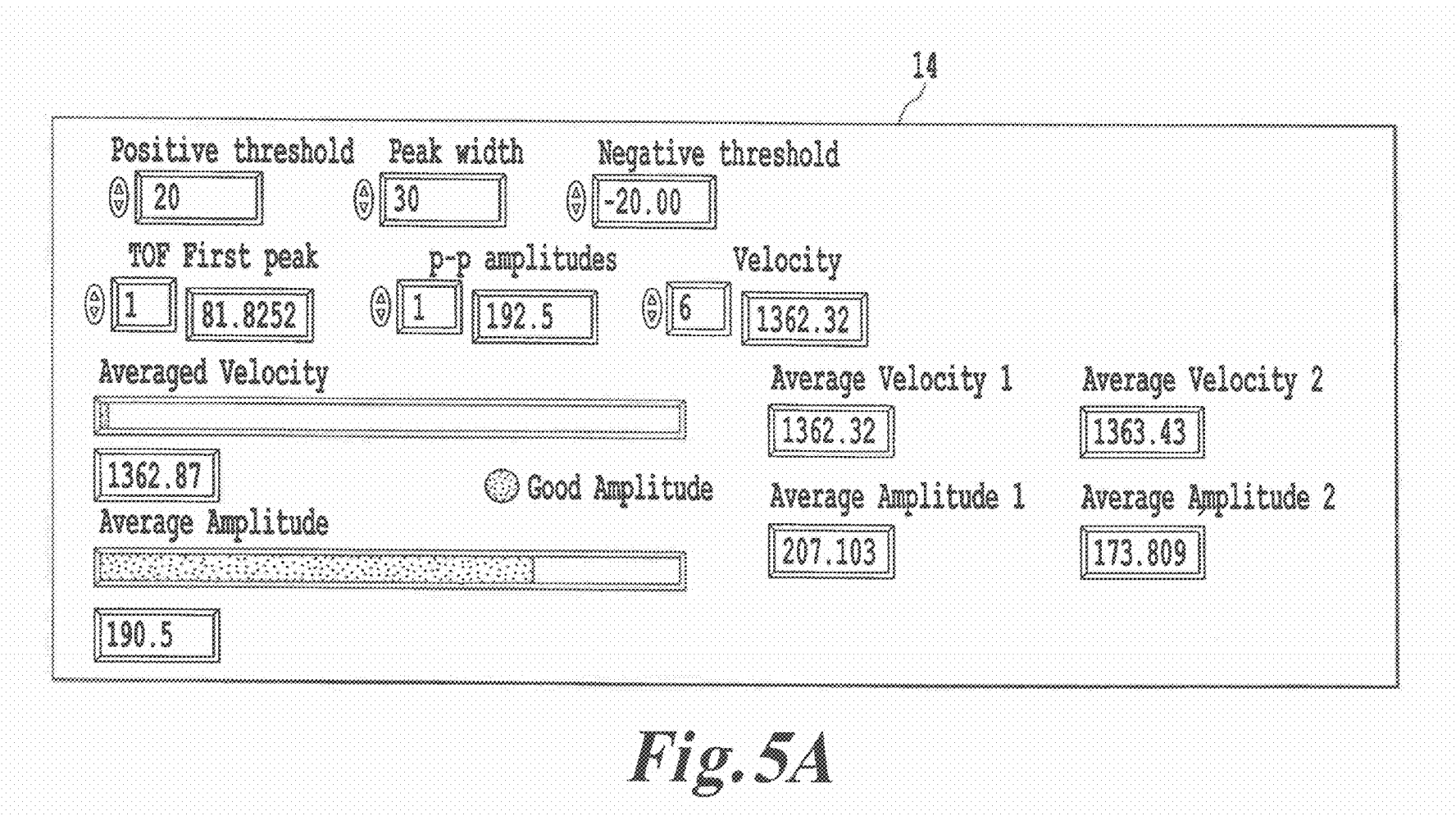
Figure 5B:
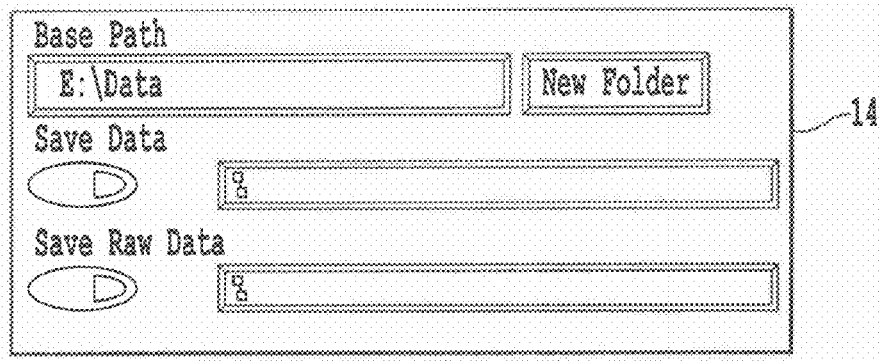
FIG. 5B is a detail of the graphical user interface of FIGS. 3A and 3B including a data save interface according to an example embodiment of the invention.

Two save data modes are implemented as shown in FIG. 5B. The first mode, "Save Data", saves only the state vector at programmed time intervals. The second mode, labeled "Save Raw Data", saves not only the state vector but the actual signals received at each transducer. While the first "Save Data" mode is designed for the routine functionality of the flowmeter, the second mode is designed for calibration, testing, and debugging.

Experimental work shows that the propagation velocity of the ultrasound pulse depends significantly on the temperature of oil-water mixture. Temperature compensation equations have been established which are effective in the range of 20-45° C. Since the temperature variation on an actual oil field can be even larger, the domain of the equations was extended to span from 0° C. to 100° C.

Figure 6:
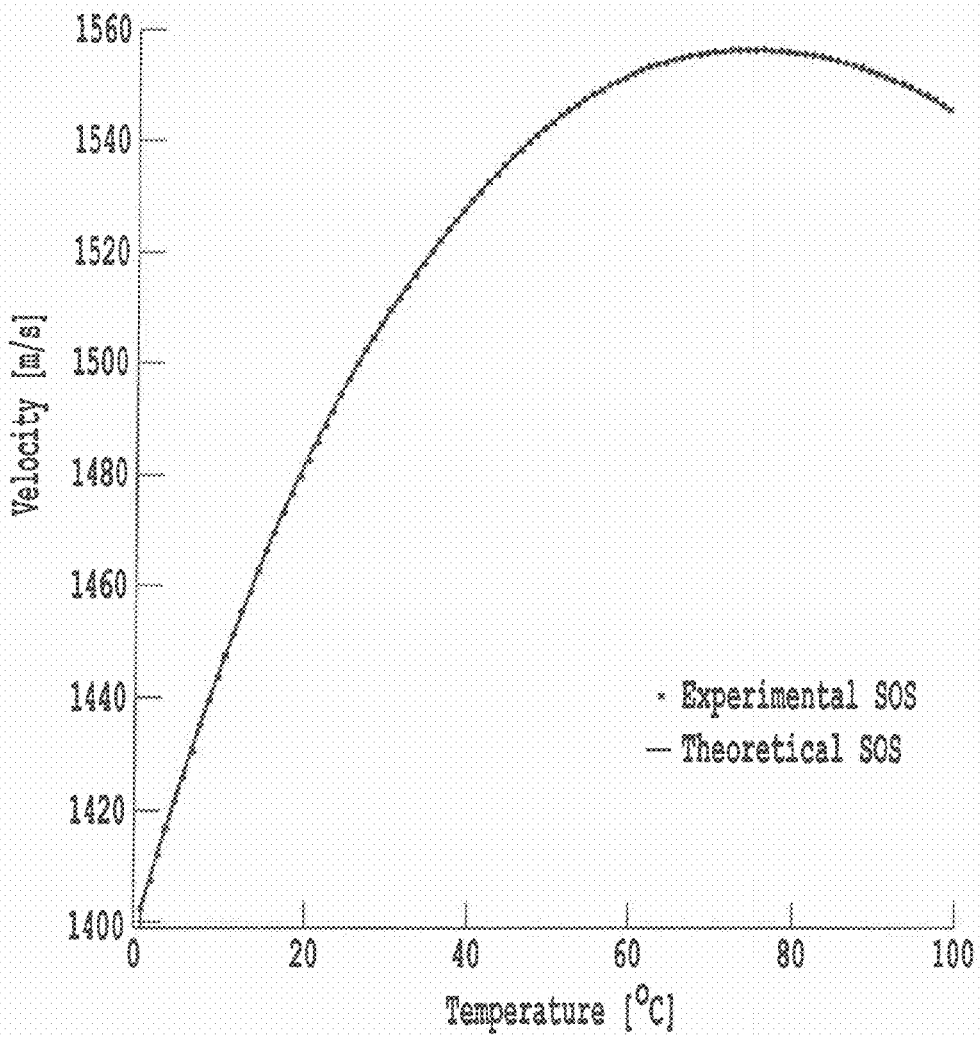
FIG. 6 is a graph showing the dependence of the ultrasound pulse velocity versus temperature in water.

Nonlinear behavior is readily apparent for such a large temperature interval as shown in FIG. 6. In general it is accepted that the speed of sound (SOS) in liquids increases with temperature. Nevertheless, for temperatures larger than 75° C. this behavior changes significantly as is shown in FIG. 6, and the SOS actually decreases as temperature increases. The ultrasound velocity has a large variation, approx 155 m/s, which is larger than the difference in velocity between the two media under consideration (water and oil). Thus, the effective compensation of the temperature effect is beneficial for precise measurements of water cuts.

In order to quantify the temperature effect on the wave velocity, a fifth order polynomial regression was performed on the experimental data, obtaining:

$$V_w(T)=k_0+k_1 T+k_2 T^2+k_3 T^3+k_4 T^4+k_5 T^5 \qquad \text{Eq. 1}$$

Where $V_w(T)$ is the ultrasound wave velocity, T is the temperature in ° C., and $k_0=1402.4\pm0.0161$
$k_1=5.0356\pm0.00334$
$k_2=-0.057869\pm0.000212$
$k_3=0.00032952\pm5.45e-06$
$k_4=-1.4563e-06\pm6.07e-08$
$k_5=3.2042e-09\pm2.44e-10$ are the calculated regression coefficients. See FIG. 6. The chi-squared test, which indicates how close a mathematical expression represents a data set, provides a value of $\chi^2=0.079760$, and reflects excellent agreement of the model with the experimental data. The corresponding temperature dependence curve was also plotted in FIG. 6 as a solid line. The approximation error is in general less than 0.25 m/s which corresponds to a percentage error of only 0.015%.

This mathematical expression can be used to correlate the ultrasound wave velocity at any desired temperature with the velocity measured at a known experimental temperature, i.e., the expression adjusts the value of the ultrasound wave velocity to compensate for the change of speed of sound due to temperature differences. Such an adjustment effectively eliminates the undesired temperature effect on wave velocity measurements, thus enhancing the accuracy of the water fraction estimation. In order to obtain an expression useful for temperature correction two different temperatures are considered: $T_0$ (the standard temperature) and $T_1$ (the temperature at which the experiments are taking place). The wave velocity for the two temperatures are written as, $$V_w(T_0)=k_0+k_1 T_0+k_2 T_0^2+k_3 T_0^3+k_4 T_0^4+k_5 T_0^5$$

$$V_w(T_1)=k_0+k_1 T_1+k_2 T_1^2+k_3 T_1^3+k_4 T_1^4+k_5 T_1^5$$

By subtracting the two equations the following equation is obtained, $$V_w(T_0)-V_w(T_1)=k_1(T_0-T_1)+k_2(T_0^2-T_1^2)+k_3(T_0^3-T_1^3)+k_4(T_0^4-T_1^4)+k_5(T_0^5-T_1^5)$$

and solving for $V_w(T_0)$, $$V_w(T_0)=V_w(T_1)+k_1(T_0-T_1)+k_2(T_0^2-T_1^2)+k_3(T_0^3-T_1^3)+k_4(T_0^4-T_1^4)+k_5(T_0^5-T_1^5)$$

Since the standard temperature is a constant, the terms containing $T_0$ may be grouped as the value $K_0$ as follows, $$V_w(T_0)=V_w(T_1)-k_1 T_1-k_2 T_1^2 k_3 T_1^3-k_4 T_1^4-k_5 T_1^5+K_0 \qquad \text{Eq. 2}$$

with $$K_0=k_1 T_0+k_2 T_0^2 k_3 T_0^3+k_4 T_0^4+k_5 T_0^5.$$

If the standard temperature is chosen as $T_0=40°$ C., then $K_0$ becomes $K_0=126.508$.

Equation 2 can now be used to calculate the wave velocity at the standard temperature $T_0$ when the experimental data were measured at a different temperature $T_1$.

Figure 7:
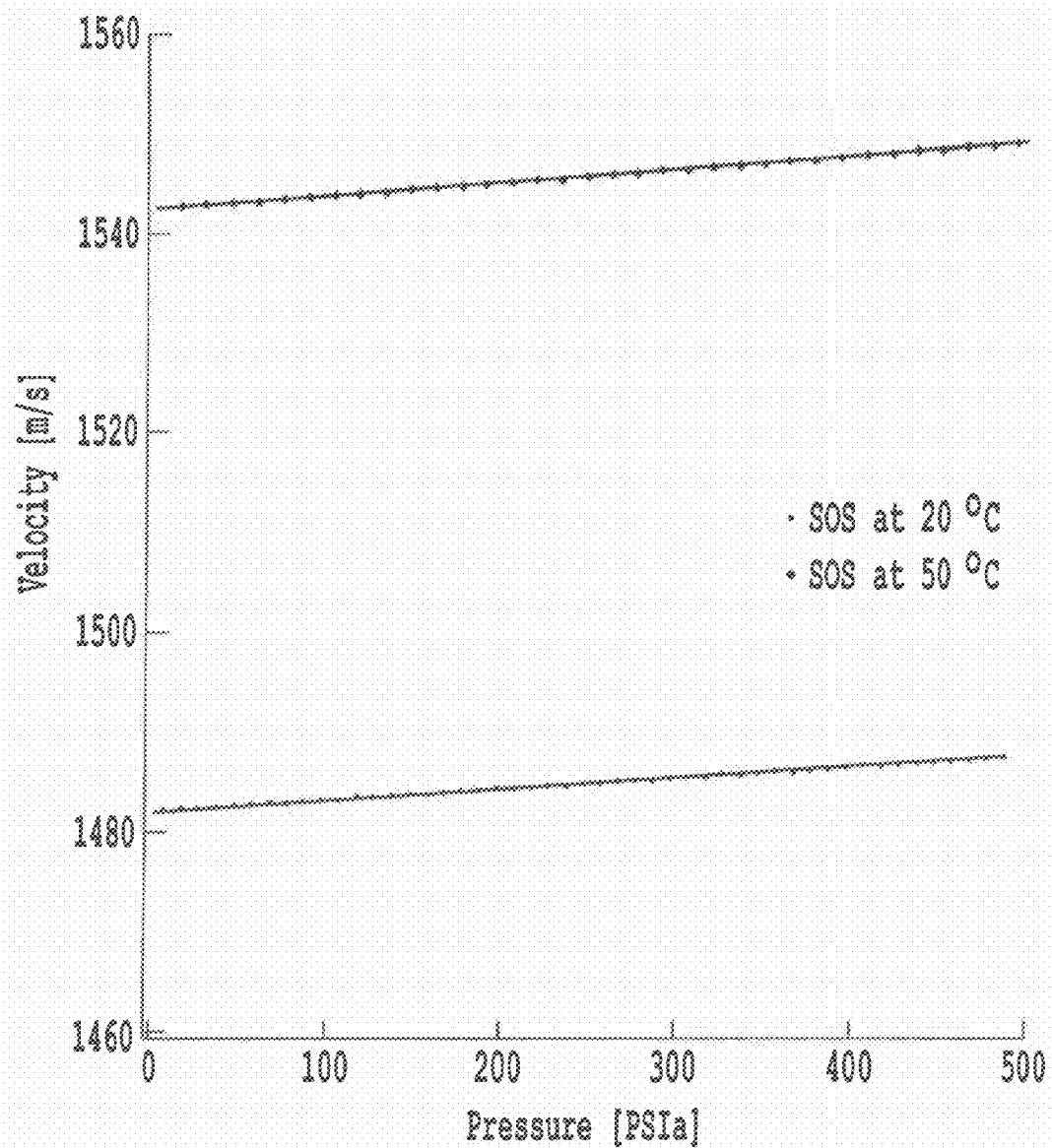
FIG. 7 is a graph showing the pressure dependence of the ultrasound wave velocity.

Another important factor that may influence the ultrasound velocity is the pressure of the liquid. FIG. 7 shows the ultrasound pulse velocity versus pressure at two different temperatures: 20° C. and 50° C. It is apparent that the velocity dependence on pressure is relatively linear for a large range of pressures (0 to 500 psia), that covers the current practical oilfield working values. Moreover, the slope of the regression line is similar even for large variations in temperatures. Even though the pressure effect is not as strong as that of temperature, it is significant and is preferably taken into account when obtaining precise measurements of the water fraction.

Figure 8:
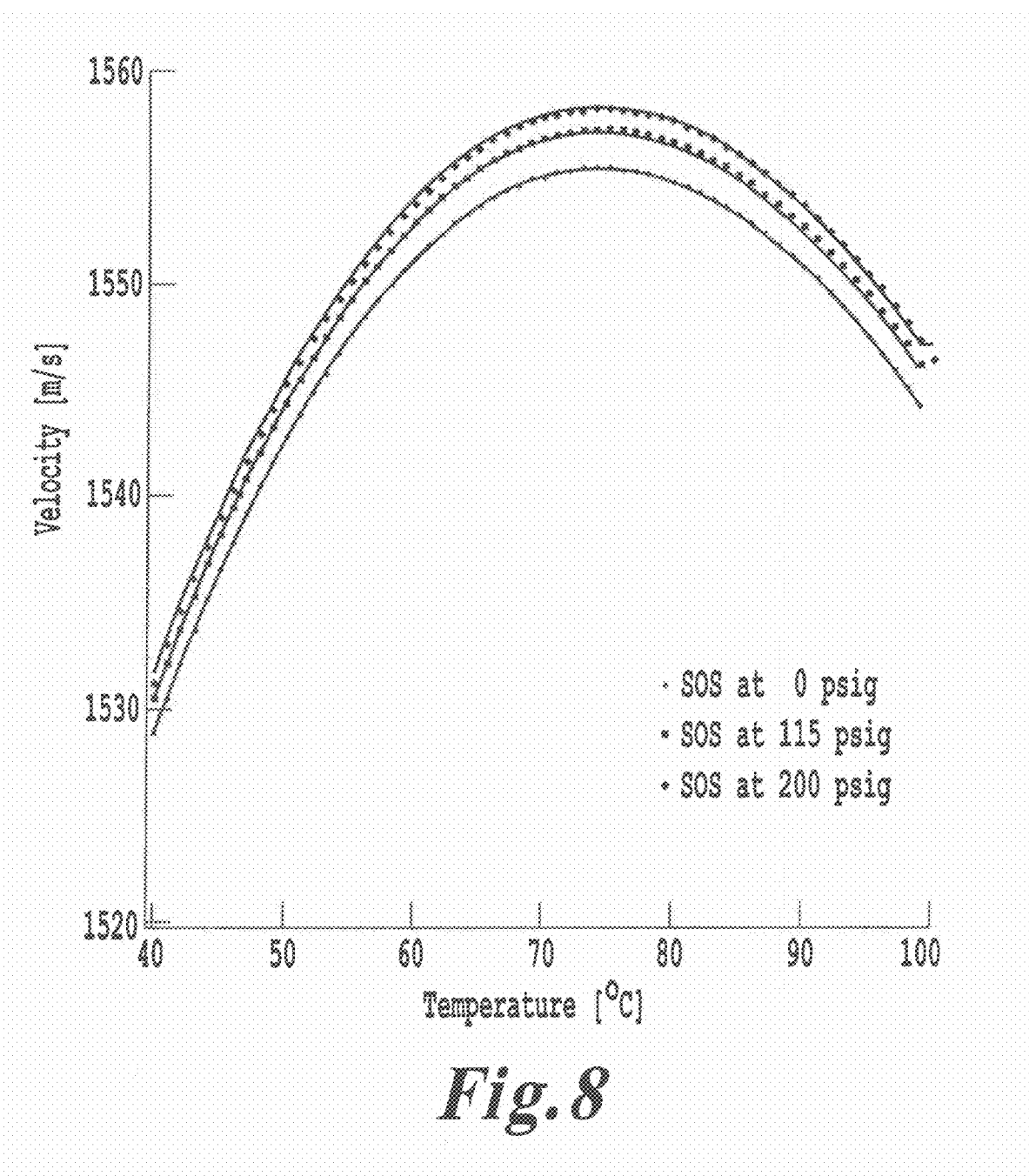
FIG. 8 is a graph showing the temperature and pressure dependence of ultrasound wave velocity.

In practice, the combined effect of both pressure and temperature are preferably addressed in the determination of the phase fractions and flow rates of oil, gas, and water in a multiphase flow stream. The three curves presented in FIG. 8 represent the temperature dependence of the wave velocity for pressures varying from 0 to 200 psig. The temperature range presented in the figure was restricted between 40 and 100° C. as being particularly relevant for the working conditions of an oilfield. Nevertheless the range of the theoretical expressions and experimental data extend from 0 to 100° C.

In order to compensate for the effect of pressure, an additional factor is added to equation 1. The equation becomes, $$V_w(T)=k_0+k_1 T+k_2 T^2+k_3 T^{3}+k_4 T^4+k_5 T^5+k_p P \qquad \text{Eq. 3}$$

where P is the pressure measured in PSIg and the pressure coefficient $k_p=0.014$ is determined experimentally.

The excellent agreement of Eq. 3 with experimental data is apparent in FIG. 8 where the dots represent the experimental data and the continuous lines are the approximating mathematical expressions. The errors for all data, from 0° C. to 100° C. are smaller than 0.1%. In order to correct the experimental data for both parameters one can first calculate the pressure compensation factor, $$Kp=k_p(P_0-P)$$

based on the actual measured pressure P and the standard pressure $P_0$, then apply equation 2 to determine the wave velocity at standard temperature. This procedure was followed in the analysis of all the experimental data.

Experimental Testing in a Full-scale Flow Loop

Extensive testing was performed in a full scale flow loop in a Multiphase Flow Laboratory. The loop has the ability to provide a total flow up to 8000 bpd of multiphase product and to inject up to 50% gas fraction. In the following description of testing, the liquid phase was a mixture of Diesel and water, and the gas phase was nitrogen.

Water Cut Measurements

In order to determine the percentage of water in the oil-water-gas mixture the ultrasound wave propagation velocity is first accurately determined. The temperature and pressure were simultaneously recorded in the following experiments since these values affect the wave velocity. Then, proper pressure and temperature compensation was applied according to the formulation shown above. A set of 23 experiments was conducted involving mixtures of Diesel and water at different concentrations. The time of flight was measured for the four channels of each detector, and the average was used to calculate the ultrasound wave velocity. The flow through the loop was varied from 2500 to 8000 bpd, and five data sets were acquired per flow rate. Table 1 shows the experimental conditions and the measured ultrasound velocities. The values for the water cut and mass flow were provided by the test loop instrumentation. The temperature and pressure values were recorder by the sensors T1 and P1. The measurement for the 100% water was done in the laboratory, prior to the field experiments.

TABLE 1

Experimental data for different water fractions.

| Exp | Water Cut [%] | Flow [lb/min] | Pressure [PSIg] | Temp [° C.] | V1 [m/s] | V2 [m/s] | V3 [m/s] | V4 [m/s] | V5 [m/s] |
|---|---|---|---|---|---|---|---|---|---|
| 1 | 93.3512 | 610.932 | 196.522 | 39.921 | 1476.9 | 1476.35 | 1476.99 | 1476.79 | 1477.47 |
| 2 | 89.3916 | 944.969 | 193.408 | 40.279 | 1475.42 | 1475.73 | 1469.54 | 1473.2 | 1474.56 |
| 3 | 88.2417 | 1409.21 | 186.111 | 42.075 | 1474.4 | 1476.95 | 1475.32 | 1474.24 | 1476.68 |
| 4 | 85.3726 | 1863.5 | 170.86 | 42.272 | 1467.96 | 1469.35 | 1472.34 | 1470.38 | 1471.42 |
| 5 | 78.7691 | 572.958 | 182.508 | 42.043 | 1454.61 | 1452.93 | 1456.25 | 1453.22 | 1455.57 |
| 6 | 75.6754 | 938.935 | 191.255 | 42.545 | 1452.36 | 1451.88 | 1452.64 | 1453.75 | 1450.24 |

TABLE 1-continued

Experimental data for different water fractions.

| Exp | Water Cut [%] | Flow [lb/min] | Pressure [PSIg] | Temp [° C.] | V1 [m/s] | V2 [m/s] | V3 [m/s] | V4 [m/s] | V5 [m/s] |
|---|---|---|---|---|---|---|---|---|---|
| 7 | 76.0026 | 1380.34 | 180.264 | 42.641 | 1450.49 | 1449.56 | 1449.24 | 1450.38 | 1449.62 |
| 8 | 73.1397 | 1845.29 | 167.684 | 42.983 | 1444.65 | 1446.93 | 1444.49 | 1448.32 | 1445.95 |
| 9 | 43.4616 | 557.824 | 192.11 | 44.826 | 1380.46 | 1378.98 | 1381.21 | 1376.05 | 1382.67 |
| 10 | 49.4808 | 885.374 | 190.614 | 45.564 | 1388.78 | 1391.26 | 1392.19 | 1387.4 | 1388.91 |
| 11 | 46.647 | 1311.74 | 179.958 | 48.321 | 1385.94 | 1384.3 | 1388.35 | 1389.42 | 1389.2 |
| 12 | 30.3514 | 537.335 | 200.034 | 44.249 | 1348.27 | 1350.73 | 1351.48 | 1352.07 | 1349.14 |
| 13 | 25.7556 | 861.36 | 196.202 | 44.378 | 1344.51 | 1345.88 | 1342.23 | 1344.19 | 1350.41 |
| 14 | 21.9624 | 1253.07 | 183.516 | 46.654 | 1339.22 | 1340.38 | 1338.94 | 1339.82 | 1336.07 |
| 15 | 21.7098 | 1599.17 | 180.676 | 48.048 | 1346.37 | 1346.85 | 1345.63 | 1345.16 | 1346.21 |
| 16 | 10.7222 | 521.125 | 195.072 | 48.043 | 1329.24 | 1328.05 | 1330.87 | 1331.04 | 1330.84 |
| 17 | 9.43934 | 824.633 | 192.446 | 48.139 | 1328.84 | 1327.42 | 1328.52 | 1329.84 | 1328.38 |
| 18 | 10.2833 | 1217.12 | 182.966 | 48.39 | 1326.45 | 1326.82 | 1325.31 | 1327.08 | 1327.16 |
| 19 | 10.1669 | 1593.75 | 170.356 | 48.503 | 1326.02 | 1326.47 | 1325.94 | 1326.48 | 1326.81 |
| 20 | 0.846378 | 502.645 | 196.202 | 47.642 | 1320.11 | 1320.23 | 1320.46 | 1320.16 | 1320.04 |
| 21 | 0.874467 | 803.238 | 194.431 | 48.059 | 1317.19 | 1318.03 | 1317.29 | 1316.35 | 1317.7 |
| 22 | 0.829387 | 1198.86 | 187.21 | 48.223 | 1318.02 | 1317.56 | 1317.65 | 1317.65 | 1317.48 |
| 23 | 0.830137 | 1548.35 | 174.188 | 48.603 | 1316.09 | 1315.47 | 1315.35 | 1315.42 | 1314.84 |
| 24 | 100 | — | 105.05 | 24.7 | 1480.46 | 1482.73 | 1481.92 | 1480.63 | 1481.59 |

As seen in the table the experimental data presents a slight pressure drop at higher flow rates and relatively small variations in temperature for each data set. Since the direction of the wave propagation is perpendicular to the flow we do not expect large variations in wave velocity with the flow rate. Indeed, the differences seen in Table 1 are not large and probably mostly due to the observed changes in pressure and temperature.

The five velocity measurements V1-V5 were then averaged to obtain (Vav), and the standard deviation ($\sigma_V$) of the data set, and the standard deviation of the mean, or the standard error, ($\sigma_{Vav}$) both in natural units and as percentage were calculated as seen in Table 2. The average Vav was then used as the predictor of the true value of the velocity of the ultrasound signal. The standard deviation of the mean is the accepted measurement of the precision of measurements. Thus, the measured valued of the velocity for each experiment would be, $$Vav \pm \sigma_{Vav}$$

TABLE 2

Error analysis for ultrasound velocity for different water fractions.

| Exp | Water Cut [%] | Flow [lb/min] | Pressure [PSIg] | Temp [° C.] | Vav [m/s] | $\sigma_V$ [m/s] | $\sigma_{Vav}$ | $\sigma_{Vav}$ [%] |
|---|---|---|---|---|---|---|---|---|
| 1 | 93.3512 | 610.932 | 196.522 | 39.921 | 1476.90 | 0.4024 | 0.1799 | 0.0122 |
| 2 | 89.3916 | 944.969 | 193.408 | 40.279 | 1473.69 | 2.5186 | 1.1264 | 0.0764 |
| 3 | 88.2417 | 1409.21 | 186.111 | 42.075 | 1475.52 | 1.2573 | 0.5623 | 0.0381 |
| 4 | 85.3726 | 1863.5 | 170.86 | 42.272 | 1470.29 | 1.7176 | 0.7681 | 0.0522 |
| 5 | 78.7691 | 572.958 | 182.508 | 42.043 | 1454.52 | 1.4424 | 0.6450 | 0.0443 |
| 6 | 75.6754 | 938.935 | 191.255 | 42.545 | 1452.17 | 1.2809 | 0.5728 | 0.0394 |
| 7 | 76.0026 | 1380.34 | 180.264 | 42.641 | 1449.86 | 0.5476 | 0.2449 | 0.0169 |
| 8 | 73.1397 | 1845.29 | 167.684 | 42.983 | 1446.07 | 1.6070 | 0.7187 | 0.0497 |
| 9 | 43.4616 | 557.824 | 192.11 | 44.826 | 1379.87 | 2.5183 | 1.1262 | 0.0816 |
| 10 | 49.4808 | 885.374 | 190.614 | 45.564 | 1389.71 | 1.9618 | 0.8773 | 0.0631 |
| 11 | 46.647 | 1311.74 | 179.958 | 48.321 | 1387.44 | 2.2336 | 0.9989 | 0.0720 |
| 12 | 30.3514 | 537.335 | 200.034 | 44.249 | 1350.34 | 1.5945 | 0.7131 | 0.0528 |
| 13 | 25.7556 | 861.36 | 196.202 | 44.378 | 1345.44 | 3.0670 | 1.3716 | 0.1019 |
| 14 | 21.9624 | 1253.07 | 183.516 | 46.654 | 1338.89 | 1.6695 | 0.7466 | 0.0558 |
| 15 | 21.7098 | 1599.17 | 180.676 | 48.048 | 1346.04 | 0.6588 | 0.2946 | 0.0219 |
| 16 | 10.7222 | 521.125 | 195.072 | 48.043 | 1330.01 | 1.3157 | 0.5884 | 0.0442 |
| 17 | 9.43934 | 824.633 | 192.446 | 48.139 | 1328.60 | 0.8721 | 0.3900 | 0.0294 |
| 18 | 10.2833 | 1217.12 | 182.966 | 48.39 | 1326.56 | 0.7537 | 0.3371 | 0.0254 |
| 19 | 10.1669 | 1593.75 | 170.356 | 48.503 | 1326.34 | 0.3605 | 0.1612 | 0.0122 |
| 20 | 0.846378 | 502.645 | 196.202 | 47.642 | 1320.20 | 0.1611 | 0.0720 | 0.0055 |
| 21 | 0.874467 | 803.238 | 194.431 | 48.059 | 1317.31 | 0.6338 | 0.2835 | 0.0215 |
| 22 | 0.829387 | 1198.86 | 187.21 | 48.223 | 1317.83 | 0.4026 | 0.1800 | 0.0137 |
| 23 | 0.830137 | 1548.35 | 174.188 | 48.603 | 1315.43 | 0.4449 | 0.1990 | 0.0151 |
| 24 | 100 | — | 105.05 | 24.7 | 1481.47 | 0.9394 | 0.4201 | 0.0284 |

Figure 9:
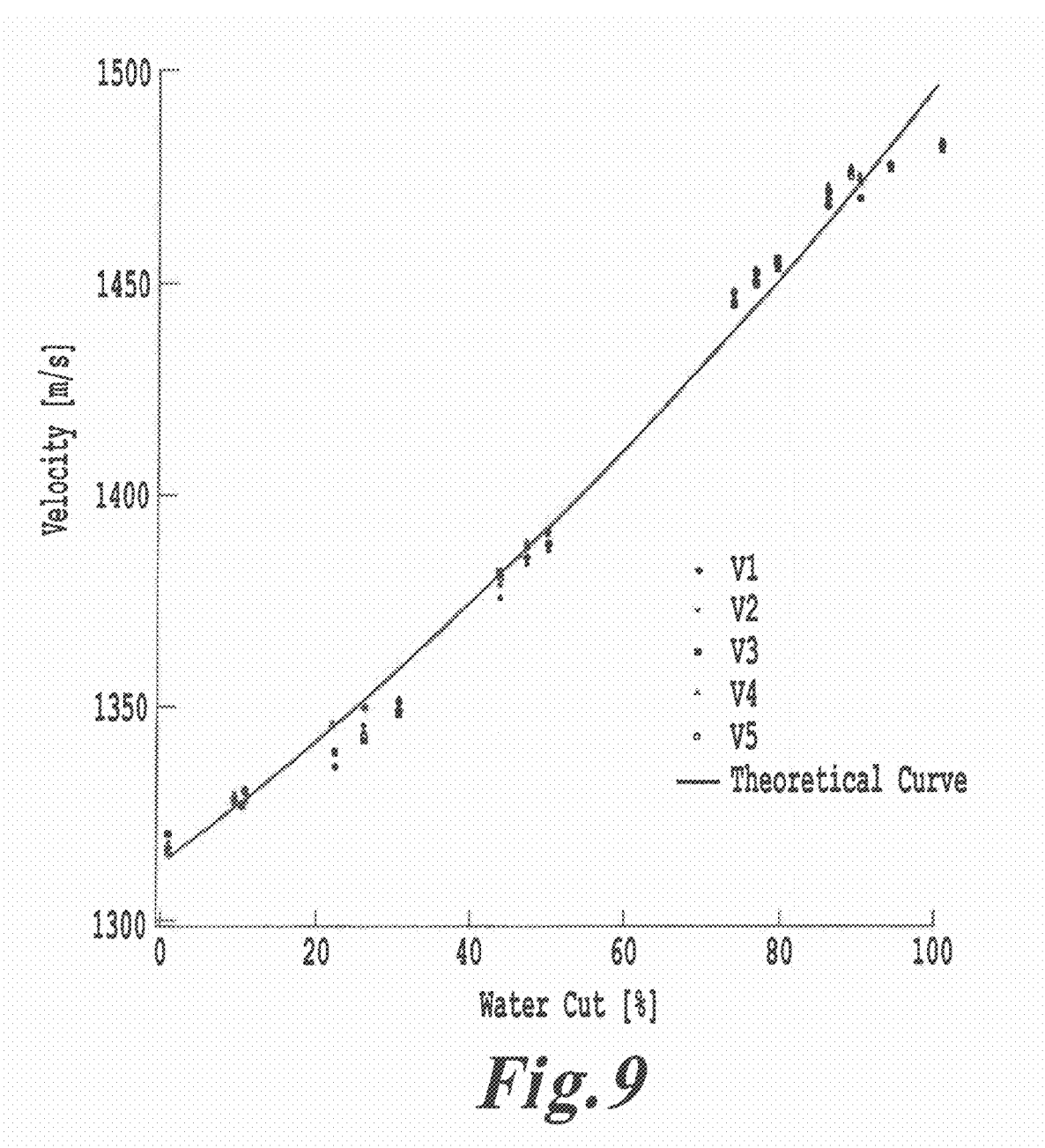
FIG. 9 is a graph showing experimental data for ultrasound velocity versus water fraction measurements.

The experimental data and a polynomial regression curve for the averaged velocities are plotted in FIG. 9. The $\chi^2=740.907$ is relatively small considering the absolute value of the experimental data, reflecting a good mathematical dependence.

The experimental data was then corrected for the effects of pressure and temperature, as described above. The values of $P_0=200$ PSIg and $T_0=40°$ C. were selected since they are closer to the actual field conditions. The results are presented in Table 3.

TABLE 3

Experimental data for different water fractions corrected for pressure and temperature effects.

| Exp | Water Cut [%] | Flow [lb/min] | Pressure [PSIg] | Temp [° C.] | Vc1 [m/s] | Vc2 [m/s] | Vc3 [m/s] | Vc4 [m/s] | Vc5 [m/s] |
|---|---|---|---|---|---|---|---|---|---|
| 1 | 93.3512 | 610.932 | 196.522 | 39.921 | 1477.08 | 1476.53 | 1477.17 | 1476.97 | 1477.65 |
| 2 | 89.3916 | 944.969 | 193.408 | 40.279 | 1475.05 | 1475.36 | 1469.17 | 1472.83 | 1474.19 |
| 3 | 88.2417 | 1409.21 | 186.111 | 42.075 | 1471.28 | 1473.83 | 1472.2 | 1471.12 | 1473.56 |
| 4 | 85.3726 | 1863.5 | 170.86 | 42.272 | 1464.76 | 1466.15 | 1469.14 | 1467.18 | 1468.22 |
| 5 | 78.7691 | 572.958 | 182.508 | 42.043 | 1451.59 | 1449.91 | 1453.23 | 1450.2 | 1452.55 |
| 6 | 75.6754 | 938.935 | 191.255 | 42.545 | 1448.46 | 1447.98 | 1448.74 | 1449.85 | 1446.34 |
| 7 | 76.0026 | 1380.34 | 180.264 | 42.641 | 1446.6 | 1445.67 | 1445.35 | 1446.49 | 1445.73 |
| 8 | 73.1397 | 1845.29 | 167.684 | 42.983 | 1440.42 | 1442.7 | 1440.26 | 1444.09 | 1441.72 |
| 9 | 43.4616 | 557.824 | 192.11 | 44.826 | 1373.26 | 1371.78 | 1374.01 | 1368.85 | 1375.47 |
| 10 | 49.4808 | 885.374 | 190.614 | 45.564 | 1380.6 | 1383.08 | 1384.01 | 1379.22 | 1380.73 |
| 11 | 46.647 | 1311.74 | 179.958 | 48.321 | 1374.44 | 1372.8 | 1376.85 | 1377.92 | 1377.7 |
| 12 | 30.3514 | 537.335 | 200.034 | 44.249 | 1341.76 | 1344.22 | 1344.97 | 1345.56 | 1342.63 |
| 13 | 25.7556 | 861.36 | 196.202 | 44.378 | 1337.87 | 1339.24 | 1335.59 | 1337.55 | 1343.77 |
| 14 | 21.9624 | 1253.07 | 183.516 | 46.654 | 1329.72 | 1330.88 | 1329.44 | 1330.32 | 1326.57 |
| 15 | 21.7098 | 1599.17 | 180.676 | 48.048 | 1335.19 | 1335.67 | 1334.45 | 1333.98 | 1335.03 |
| 16 | 10.7222 | 521.125 | 195.072 | 48.043 | 1317.86 | 1316.67 | 1319.49 | 1319.66 | 1319.46 |
| 17 | 9.43934 | 824.633 | 192.446 | 48.139 | 1317.38 | 1315.96 | 1317.06 | 1318.38 | 1316.92 |
| 18 | 10.2833 | 1217.12 | 182.966 | 48.39 | 1314.83 | 1315.2 | 1313.69 | 1315.46 | 1315.54 |
| 19 | 10.1669 | 1593.75 | 170.356 | 48.503 | 1314.44 | 1314.89 | 1314.36 | 1314.9 | 1315.23 |
| 20 | 0.846378 | 502.645 | 196.202 | 47.642 | 1309.2 | 1309.32 | 1309.55 | 1309.25 | 1309.13 |
| 21 | 0.874467 | 803.238 | 194.431 | 48.059 | 1305.8 | 1306.64 | 1305.9 | 1304.96 | 1306.31 |
| 22 | 0.829387 | 1198.86 | 187.21 | 48.223 | 1306.54 | 1306.97 | 1306.08 | 1306.17 | 1306 |
| 23 | 0.830137 | 1548.35 | 174.188 | 48.603 | 1304.34 | 1303.72 | 1303.6 | 1303.67 | 1303.09 |
| 24 | 100 | — | 105.05 | 24.7 | 1514.78 | 1517.05 | 1516.24 | 1514.95 | 1515.91 |

Table 4 presents the pressure and temperature compensated averaged velocities and the error analysis. As expected the change in the standard error is very small since the compensation procedure implies mathematical operations with exact numbers.

TABLE 4

Error analysis for ultrasound velocity for different water fractions.

| Exp | Water Cut [%] | Flow [lb/min] | Pressure [PSIg] | Temp [° C.] | Vav [m/s] | $\sigma_V$ [m/s] | $\sigma_{Vav}$ | $\sigma_{Vav}$ [%] |
|---|---|---|---|---|---|---|---|---|
| 1 | 93.3512 | 610.932 | 196.522 | 39.921 | 1477.08 | 0.4024 | 0.1799 | 0.0122 |
| 2 | 89.3916 | 944.969 | 193.408 | 40.279 | 1473.32 | 2.5186 | 1.1264 | 0.0765 |
| 3 | 88.2417 | 1409.21 | 186.111 | 42.075 | 1472.40 | 1.2573 | 0.5623 | 0.0382 |
| 4 | 85.3726 | 1863.5 | 170.86 | 42.272 | 1467.09 | 1.7176 | 0.7681 | 0.0524 |
| 5 | 78.7691 | 572.958 | 182.508 | 42.043 | 1451.50 | 1.4424 | 0.6450 | 0.0444 |
| 6 | 75.6754 | 938.935 | 191.255 | 42.545 | 1448.27 | 1.2809 | 0.5728 | 0.0396 |
| 7 | 76.0026 | 1380.34 | 180.264 | 42.641 | 1445.97 | 0.5476 | 0.2449 | 0.0169 |
| 8 | 73.1397 | 1845.29 | 167.684 | 42.983 | 1441.84 | 1.6070 | 0.7187 | 0.0498 |
| 9 | 43.4616 | 557.824 | 192.11 | 44.826 | 1372.67 | 2.5183 | 1.1262 | 0.0820 |
| 10 | 49.4808 | 885.374 | 190.614 | 45.564 | 1381.53 | 1.9618 | 0.8773 | 0.0635 |
| 11 | 46.647 | 1311.74 | 179.958 | 48.321 | 1375.94 | 2.2336 | 0.9989 | 0.0726 |
| 12 | 30.3514 | 537.335 | 200.034 | 44.249 | 1343.83 | 1.5945 | 0.7131 | 0.0531 |
| 13 | 25.7556 | 861.36 | 196.202 | 44.378 | 1338.80 | 3.0670 | 1.3716 | 0.1024 |
| 14 | 21.9624 | 1253.07 | 183.516 | 46.654 | 1329.39 | 1.6695 | 0.7466 | 0.0562 |
| 15 | 21.7098 | 1599.17 | 180.676 | 48.048 | 1334.86 | 0.6588 | 0.2946 | 0.0221 |
| 16 | 10.7222 | 521.125 | 195.072 | 48.043 | 1318.63 | 1.3157 | 0.5884 | 0.0446 |
| 17 | 9.43934 | 824.633 | 192.446 | 48.139 | 1317.14 | 0.8721 | 0.3900 | 0.0296 |
| 18 | 10.2833 | 1217.12 | 182.966 | 48.39 | 1314.94 | 0.7537 | 0.3371 | 0.0256 |
| 19 | 10.1669 | 1593.75 | 170.356 | 48.503 | 1314.76 | 0.3605 | 0.1612 | 0.0123 |
| 20 | 0.846378 | 502.645 | 196.202 | 47.642 | 1309.29 | 0.1611 | 0.0720 | 0.0055 |
| 21 | 0.874467 | 803.238 | 194.431 | 48.059 | 1305.92 | 0.6338 | 0.2835 | 0.0217 |
| 22 | 0.829387 | 1198.86 | 187.21 | 48.223 | 1306.35 | 0.4026 | 0.1800 | 0.0138 |
| 23 | 0.830137 | 1548.35 | 174.188 | 48.603 | 1303.68 | 0.4449 | 0.1990 | 0.0153 |
| 24 | 100 | — | 105.05 | 24.7 | 1515.79 | 0.9394 | 0.4201 | 0.0277 |

Figure 10:
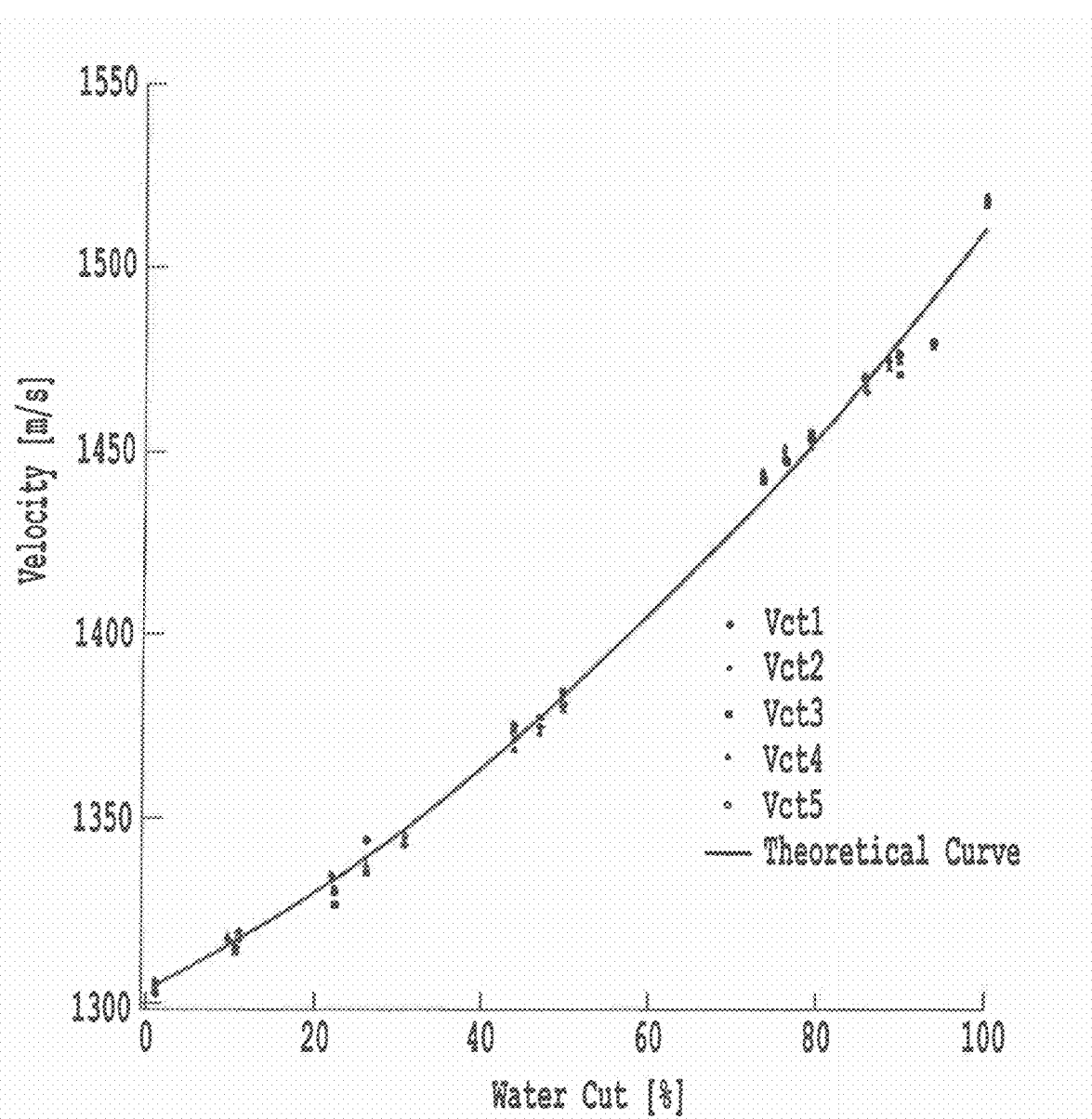
FIG. 10 is a graph showing experimental data for water fractions measurements corrected for pressure and temperature effects.

As can be seen in Tables 3, 4, and FIG. 10, after the pressure and temperature corrections, the differences between the velocities measured at different flow rates are reduced in magnitude. A quadratic regression was performed on the averaged values of the wave velocities, expressed as, $$V_w(wc) = k_0 + k_1 wc + k_2 wc^2$$

Where $V_w(wc)$ is the wave velocity, wc is the water fraction in %. The regression coefficients were obtained as, $$k_0 = 1304.2 \pm 1.81$$

$$k_1 = 1.1453 \pm 0.109$$

$$k_2 = 0.008942 \pm 0.00112$$

The value of $\chi^2 = 387.449$ is almost twice as small as the value obtained for the same type of regression for the uncorrected data. It reflects excellent agreement of the model with the experimentally measured data. This expression can be used to calculate the ultrasound wave velocity that we expect to measure for a certain water fraction at a certain temperature and pressure.

Since it is desirable to determine the amount of water in the mixture (for example, an oil, water, and gas mixture), one calculates the water cut from a measured wave velocity. Solving the quadratic equation for water cut wc we obtain the following water cut determination equation:

$$wc = \frac{-k_1 + \sqrt{k_1^2 - 4k_2(k_0 + V_w)}}{2k_2}$$

Substituting the numerical values for $k_0$, $k_1$, and $k_2$ we arrived at the following expression, $$wc = 55.9159\sqrt{0.035768 V_w - 45.3369} - 64.0405 \quad \text{Eq. 4}$$

Figure 11:
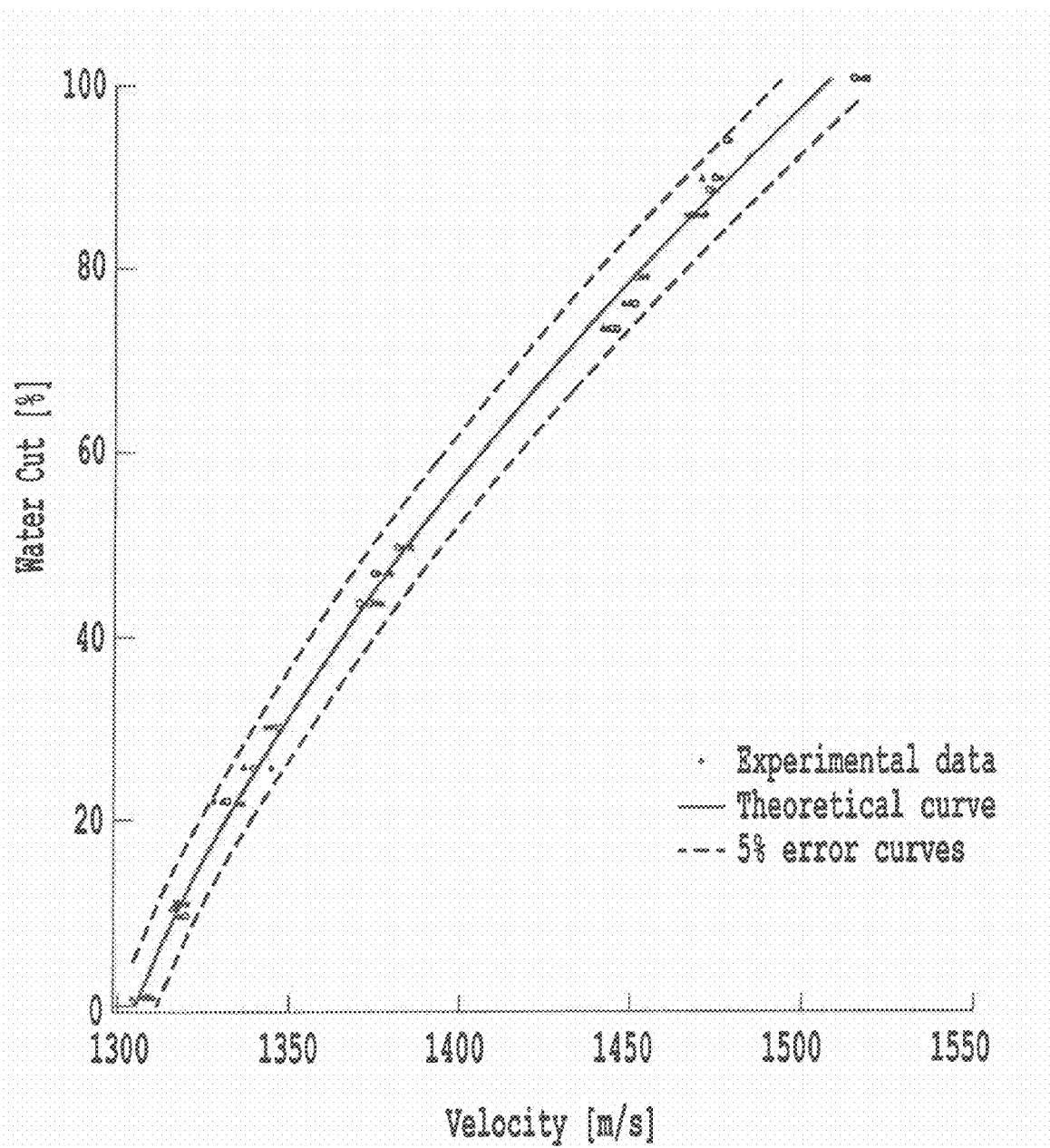
FIG. 11 is a graph showing experimental data and theoretical curve for water cut versus ultrasound wave velocity.

Equation 4 can be used to determine the water cut in the water-oil liquid mixture, based on the measured wave velocity. The experimental data, the theoretical curve obtained using Equation 4, and ±5% error curves are presented in FIG. 11. All experimental data are included in the ±5% error range, with most data points presenting less then 3% error from the theoretical curve. Thus, the UPFD 1 proved to have good precision and accuracy in experimental conditions that simulate the actual oilfield environment.

Gas Fraction Measurements

Research has shown that the gas volumetric fraction in an oil-water-gas mixture is exponentially correlated with the attenuation of the ultrasound wave. In order to determine the wave attenuation, one measures the amplitude of the wave that propagates from the ultrasound transmitter to the sensor array 6 positioned on an opposing wall of the UPFD 1.

A set of 10 experiments was conducted involving two mixtures of diesel and water at 25% and a set of 5 experiments at 50% water cut. The flow through the loop was varied from 4000 to 6000 bpd, and the gas volumetric fraction (GVF) was set at 0%, 10%, 20%, 30%, 40%, and 50%. The actual values for the GVF, water cut, and the flow rates were measured by the test loop equipment. The experimental data represents 3 minute averages of the measured values. Pressure and temperatures were measured by dedicated sensors. The amplitude of an average of 50 ultrasound signals was determined for each channel of the detector, and then averaged for the eight channels of the flowmeter.

Figure 12:
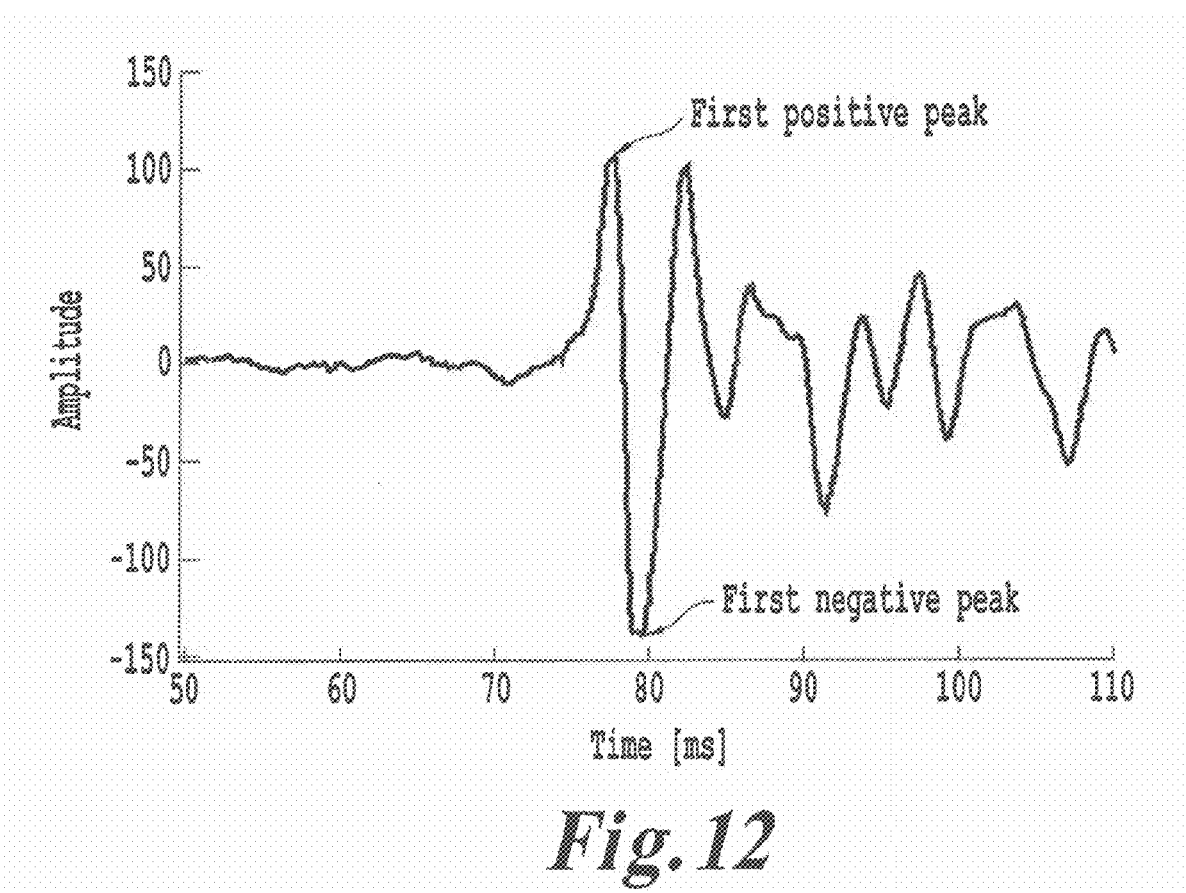
FIG. 12 is a graph showing peak detection for calculation of the ultrasound signal amplitude.

For this purpose the amplitude of the ultrasound signal is determined by detecting the first positive and first negative peaks on the recorded signal and calculates the amplitude. FIG. 12. A "Good Amplitude" test is performed by checking for signal clipping and for a time differential between positive and the negative peaks. The transmitter voltage was adjusted such that no clipping occurred. For calibration purposes, only a predetermined set of values for the transmitter voltages were allowed: 3, 30, 50, 70, 90, and 100V.

Five data sets were acquired per each flow rate, water cut, and gas volumetric fraction combination. The temperature and pressure were simultaneously recorded, since they could affect the measurements. Table 5 shows the experimental conditions, and the measured amplitudes for the five data points A1-A5. The values of the measured amplitudes are shown as digitized by the data acquisition cards, with no physical units.

The five amplitude measurements A1-A5 were then averaged (Aav), and the standard deviation ($\sigma_A$) of the data set, and the standard deviation of the mean, or the standard error, ($\sigma_{Aav}$) both in natural units and as percentage were calculated as seen in Table 6. The average Aav was then used as the predictor of the true value of the amplitude of the transmitted ultrasound signal. The standard deviation of the mean is the accepted measurement of the precision of measurements. Thus, the measured valued of the amplitude for each experiment would be, $$Aav \pm \sigma_{Aav}$$

TABLE 5

Experimental data for different gas volumetric fractions and 25% water cut.

| Exp | GVF [%] | Water Cut [%] | Flow [lb/min] | Pressure [PSIg] | Temp [° C.] | Trans. Volt. [V] | A1 | A2 | A3 | A4 | A5 |
|---|---|---|---|---|---|---|---|---|---|---|---|
| 1 | 0 | 25.76 | 861.36 | 196.9 | 43.3 | 3 | 152.726 | 150.183 | 155.424 | 153.518 | 150.983 |
| 2 | 10.32 | 26.68 | 842.245 | 193.92 | 43.26 | 30 | 239.386 | 235.372 | 232.539 | 240.11 | 236.729 |
| 3 | 19.89 | 27.13 | 839.787 | 193.98 | 43.39 | 50 | 192.17 | 196.114 | 194.729 | 190.43 | 188.732 |

TABLE 5-continued

Experimental data for different gas volumetric fractions and 25% water cut.

| Exp | GVF [%] | Water Cut [%] | Flow [lb/min] | Pressure [PSIg] | Temp [° C.] | Trans. Volt. [V] | A1 | A2 | A3 | A4 | A5 |
|---|---|---|---|---|---|---|---|---|---|---|---|
| 4 | 29.60 | 27.31 | 856.554 | 194.05 | 43.46 | 70 | 141.827 | 143.844 | 154.223 | 139.631 | 135.583 |
| 5 | 39.66 | 27.04 | 873.406 | 189.67 | 43.94 | 90 | 82.592 | 85.693 | 81.928 | 79.381 | 80.227 |
| 6 | 48.86 | 27.05 | 834.26 | 178.51 | 44.65 | 100 | 48.391 | 52.625 | 56.582 | 53.259 | 50.271 |
| 7 | 9.495 | 22.58 | 1260.48 | 184.19 | 45.97 | 30 | 224.461 | 220.539 | 229.428 | 227.628 | 221.527 |
| 8 | 20.25 | 23.6 | 1261.54 | 184.84 | 46.01 | 50 | 172.428 | 170.893 | 168.318 | 176.253 | 178.432 |
| 9 | 29.45 | 24.15 | 1264.67 | 185.01 | 46.08 | 70 | 120.311 | 118.726 | 119.422 | 124.521 | 115.329 |
| 10 | 39.17 | 25.19 | 1256.81 | 175.37 | 46.28 | 90 | 67.752 | 71.317 | 73.672 | 68.149 | 72.483 |
| 11 | 48.26 | 26.26 | 1212.3 | 157.7 | 47.27 | 100 | 36.249 | 32.527 | 34.150 | 31.372 | 28.441 |

The standard error was less then 4% with most values being close to 1%. The larger errors correspond to the smaller recorded amplitudes, since the peak detection is more difficult and less precise in such cases. This was due to the fact that the transmitter voltage for this experiment was limited to 100V. Since the electronics may provide an excitation signal of up to 500V, and in real life measurements the automatic adjustment of the transmitter voltage would keep the detected amplitude larger than 100 digital units, the error would be smaller in a typical measurement environment. Moreover, the 50 ultrasound signals averaged to obtain each amplitude measurement were recorded and processed in less than 1 second. Since such a speed is not necessary for typical gas fraction measurements a larger number of signals could be used in calculation. This would allow enhancing the precision of the measured results.

Figure 13:
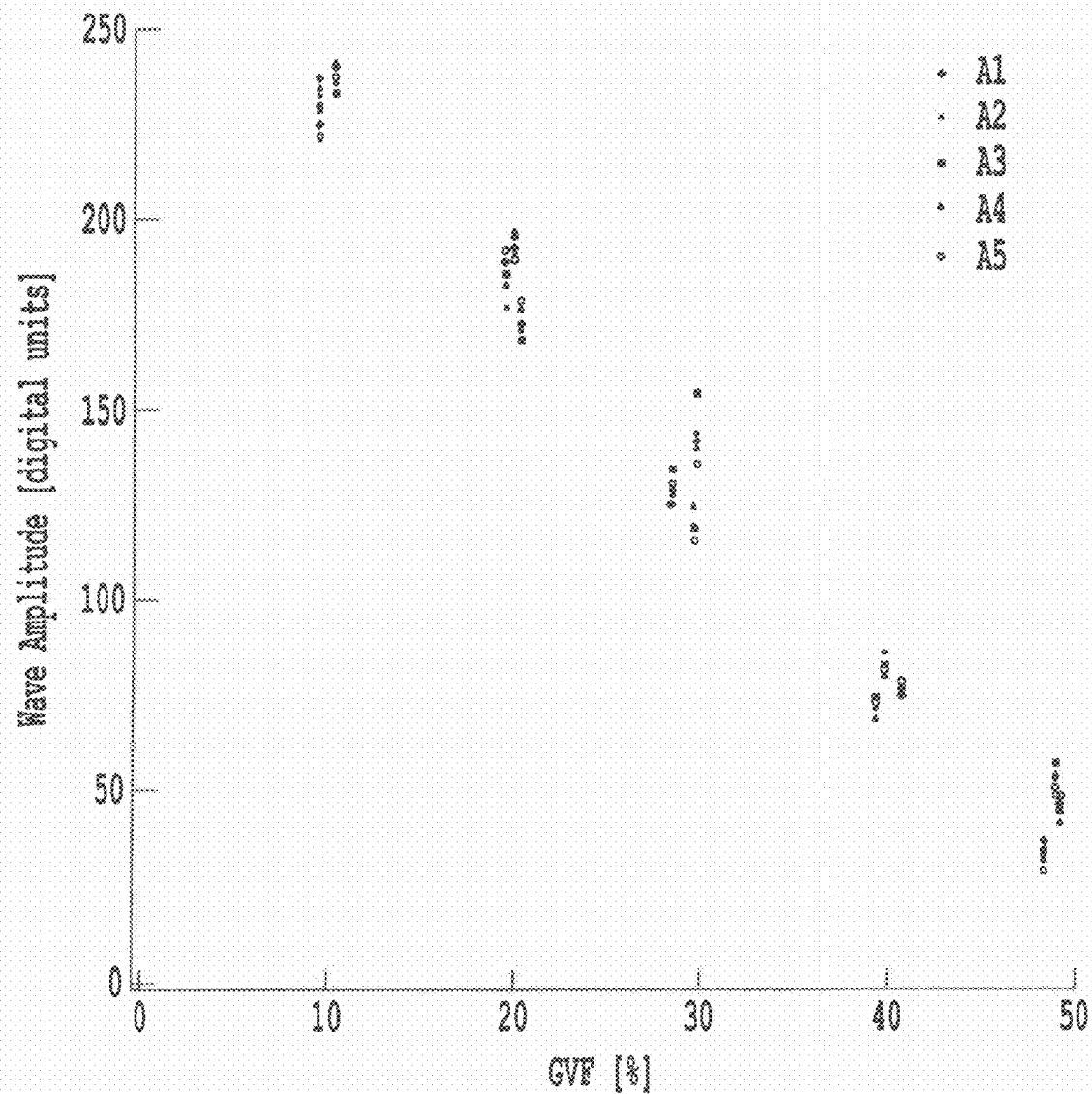
FIG. 13 is a graph showing measured ultrasound wave amplitudes versus gas volumetric fraction.

FIG. 13 shows the measured ultrasound wave amplitudes versus gas volumetric fraction. As is evident from FIG. 13, the amplitude is strongly dependent on the gas fraction.

Since the transmitter voltage changed during the measurements, the amplitude of the transmitted signal does not measure the actual attenuation of the ultrasound wave. Thus, the transmission factor $T_f$ is defined as, $$T_f = \frac{A}{GT_v} \times 1000$$

where A is the wave amplitude, G is the system gain including the preamplifier and the A/D card gains, and $T_v$ is the transmitter voltage. A proportionality factor of 1,000 was used to obtain more readable values.

Table 7 presents the data for the calculated ultrasound signal transmission factor for all the experiments, and Table 8 presents the corresponding statistics. Because the transmission factor is obtained by multiplication and divisions with exact numbers, changes in the percentage standard error are not expected, even though the actual standard deviation of the mean looks smaller. As before, the measured value of the transmission factor is, $$T_f \pm \sigma_{Tfav}$$

TABLE 6

Error analysis for amplitude measurement for different gas volumetric fractions and 25% water cut.

| Exp | GVF [%] | Water Cut [%] | Flow [lb/min] | Pressure [PSIg] | Temp [° C.] | Trans. Volt. [V] | Aav | $\sigma_A$ | $\sigma_{Aav}$ | $\sigma_{Aav}$ % |
|---|---|---|---|---|---|---|---|---|---|---|
| 1 | 0 | 25.76 | 861.36 | 196.9 | 43.3 | 3 | 152.567 | 2.08 | 0.93 | 0.61 |
| 2 | 10.32 | 26.68 | 842.245 | 193.92 | 43.26 | 30 | 236.827 | 3.08 | 1.38 | 0.58 |
| 3 | 19.89 | 27.13 | 839.787 | 193.98 | 43.39 | 50 | 192.435 | 3.02 | 1.35 | 0.70 |
| 4 | 29.60 | 27.31 | 856.554 | 194.05 | 43.46 | 70 | 143.022 | 6.97 | 3.12 | 2.18 |
| 5 | 39.66 | 27.04 | 873.406 | 189.67 | 43.94 | 90 | 81.964 | 2.45 | 1.10 | 1.34 |
| 6 | 48.86 | 27.05 | 834.26 | 178.51 | 44.65 | 100 | 52.225 | 3.11 | 1.39 | 2.66 |
| 7 | 9.495 | 22.58 | 1260.48 | 184.19 | 45.97 | 30 | 224.717 | 3.82 | 1.71 | 0.76 |
| 8 | 20.25 | 23.60 | 1261.54 | 184.84 | 46.01 | 50 | 173.265 | 4.08 | 1.82 | 1.05 |
| 9 | 29.45 | 24.15 | 1264.67 | 185.01 | 46.08 | 70 | 119.662 | 3.31 | 1.48 | 1.24 |
| 10 | 39.17 | 25.19 | 1256.81 | 175.37 | 46.28 | 90 | 70.674 | 2.63 | 1.17 | 1.66 |
| 11 | 48.26 | 26.26 | 1212.3 | 157.7 | 47.27 | 100 | 32.547 | 2.94 | 1.31 | 4.04 |

TABLE 7

Experimental data for ultrasound signal transmission factor.

| Exp | GVF [%] | Water Cut [%] | Flow [lb/min] | Pressure [PSIg] | Temp [°C.] | Tf1 | Tf2 | Tf3 | Tf4 | Tf5 |
|---|---|---|---|---|---|---|---|---|---|---|
| 1 | 0 | 25.76 | 861.36 | 196.9 | 43.3 | 19.886 | 19.555 | 20.238 | 19.989 | 19.659 |
| 2 | 10.32 | 26.68 | 842.245 | 193.92 | 43.26 | 3.117 | 3.065 | 3.028 | 3.126 | 3.082 |
| 3 | 19.89 | 27.13 | 839.787 | 193.98 | 43.39 | 1.501 | 1.532 | 1.521 | 1.488 | 1.475 |
| 4 | 29.60 | 27.31 | 856.554 | 194.05 | 43.46 | 0.791 | 0.803 | 0.861 | 0.779 | 0.757 |
| 5 | 39.66 | 27.04 | 873.406 | 189.67 | 43.94 | 0.358 | 0.372 | 0.356 | 0.345 | 0.348 |
| 6 | 48.86 | 27.05 | 834.26 | 178.51 | 44.65 | 0.189 | 0.206 | 0.221 | 0.208 | 0.196 |
| 7 | 9.495 | 22.58 | 1260.48 | 184.19 | 45.97 | 2.923 | 2.872 | 2.987 | 2.964 | 2.885 |
| 8 | 20.25 | 23.6 | 1261.54 | 184.84 | 46.01 | 1.347 | 1.335 | 1.315 | 1.377 | 1.394 |
| 9 | 29.45 | 24.15 | 1264.67 | 185.01 | 46.08 | 0.671 | 0.663 | 0.666 | 0.695 | 0.644 |
| 10 | 39.17 | 25.19 | 1256.81 | 175.37 | 46.28 | 0.294 | 0.310 | 0.320 | 0.296 | 0.315 |
| 11 | 48.26 | 26.26 | 1212.3 | 157.7 | 47.27 | 0.142 | 0.127 | 0.133 | 0.123 | 0.111 |

TABLE 8

Error analysis for ultrasound signal transmission factor.

| Exp | GVF [%] | Water Cut [%] | Flow [lb/min] | Pressure [PSIg] | Temp [°C.] | Tfav | $\sigma_{Tf}$ | $\sigma_{Tfav}$ | $\sigma_{Tfav}$ % |
|---|---|---|---|---|---|---|---|---|---|
| 1 | 0 | 25.76 | 861.36 | 196.9 | 43.3 | 19.865 | 0.2709 | 0.1211 | 0.6098 |
| 2 | 10.32 | 26.68 | 842.245 | 193.92 | 43.26 | 3.084 | 0.0400 | 0.0179 | 0.5805 |
| 3 | 19.89 | 27.13 | 839.787 | 193.98 | 43.39 | 1.503 | 0.0236 | 0.0106 | 0.7024 |
| 4 | 29.60 | 27.31 | 856.554 | 194.05 | 43.46 | 0.798 | 0.0389 | 0.0174 | 2.1799 |
| 5 | 39.66 | 27.04 | 873.406 | 189.67 | 43.94 | 0.356 | 0.0106 | 0.0048 | 1.3359 |
| 6 | 48.86 | 27.05 | 834.26 | 178.51 | 44.65 | 0.204 | 0.0122 | 0.0054 | 2.6641 |
| 7 | 9.495 | 22.58 | 1260.48 | 184.19 | 45.97 | 2.926 | 0.0497 | 0.0222 | 0.7599 |
| 8 | 20.25 | 23.6 | 1261.54 | 184.84 | 46.01 | 1.354 | 0.0318 | 0.0142 | 1.0518 |
| 9 | 29.45 | 24.15 | 1264.67 | 185.01 | 46.08 | 0.668 | 0.0185 | 0.0083 | 1.2358 |
| 10 | 39.17 | 25.19 | 1256.81 | 175.37 | 46.28 | 0.307 | 0.0114 | 0.0051 | 1.6620 |
| 11 | 48.26 | 26.26 | 1212.3 | 157.7 | 47.27 | 0.127 | 0.0115 | 0.0051 | 4.0360 |

Figure 14:
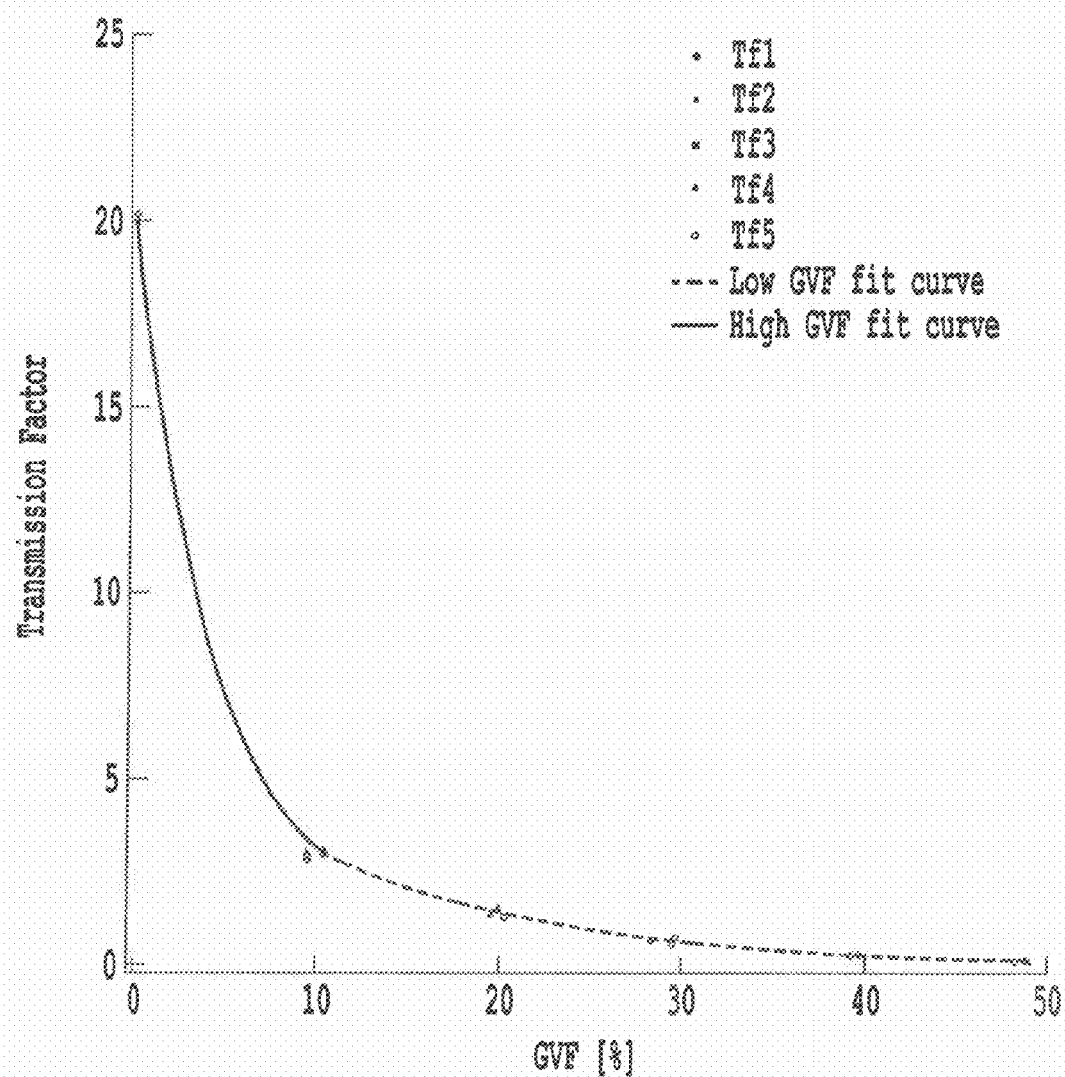
FIG. 14 is a graph showing the ultrasound transmission factor versus gas volumetric fraction.

The experimental data for the transmission factor are shown in FIG. 14 versus the gas volumetric fraction GVF. All experimental data are shown, including the ones corresponding to 50% water cut.

The dependence of the ultrasound attenuation to the GVF is exponential. Moreover, there are two different types of interaction between the ultrasound wave and the gas bubbles inside the flow stream. When the GVF is relatively low, and the gas bubbles are small compared to the wavelength, the ultrasound wave is scattered uniformly in all directions. When the GVF is large the attenuation occurs mostly by back reflection. The consequence is that there are two different measurement regimes with two corresponding mathematical models.

Thus, the average transmission factor measured for 25% water cut was used to obtain two exponential regressions, one for the 0 to just below 10% GVF and the other for 10 to 50% GVF.

For the 0 to just below 10% GVF range the theoretical curve is described by, $$T_f = k_{L0} + k_{L1} e^{-k_{L2} GVF} \qquad \text{Eq. 5}$$

where the regression coefficients were:

$k_{L0}$=1.2152±0.0881

$k_{L1}$=18.65±0.128

$k_{L2}$=0.22296±0.00727

The regression was in good agreement with the data as shown by the small chi-squared test result of $\chi^2$=0.00881634. For the 10 to 50% GVF range the regression was, $$T_f = k_{H0} + k_{H1} e^{-k_{H2} GVF} \qquad \text{Eq. 6}$$

with $k_{H0}$=0.018501±0.0618

$k_{H1}$=6.8297±0.334

Figure 15:
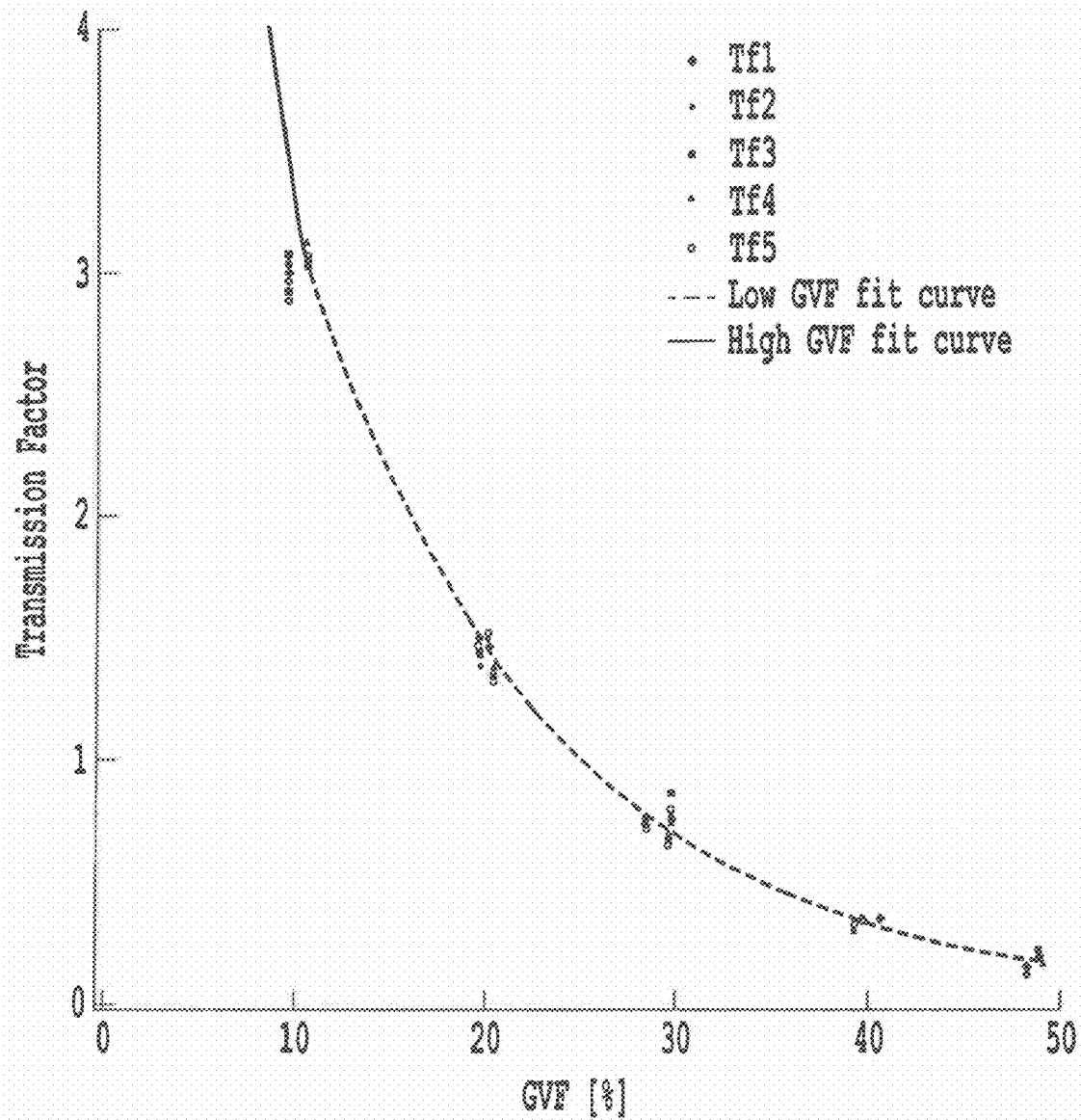
FIG. 15 is a graph showing the ultrasound transmission factor versus gas volumetric fraction in the 10 to 50% GVF range.

$k_{H2}$=0.077899±0.00495 and a chi-squared test result of $\chi^2$=0.0238425. The $\chi^2$ factor is in this case slightly larger because more experimental data were recorded in this interval. FIG. 15 presents the transmission factor for the 10 to 50% GVF range. This range is considered more relevant for the industrial applications of the meter.

Figure 16:
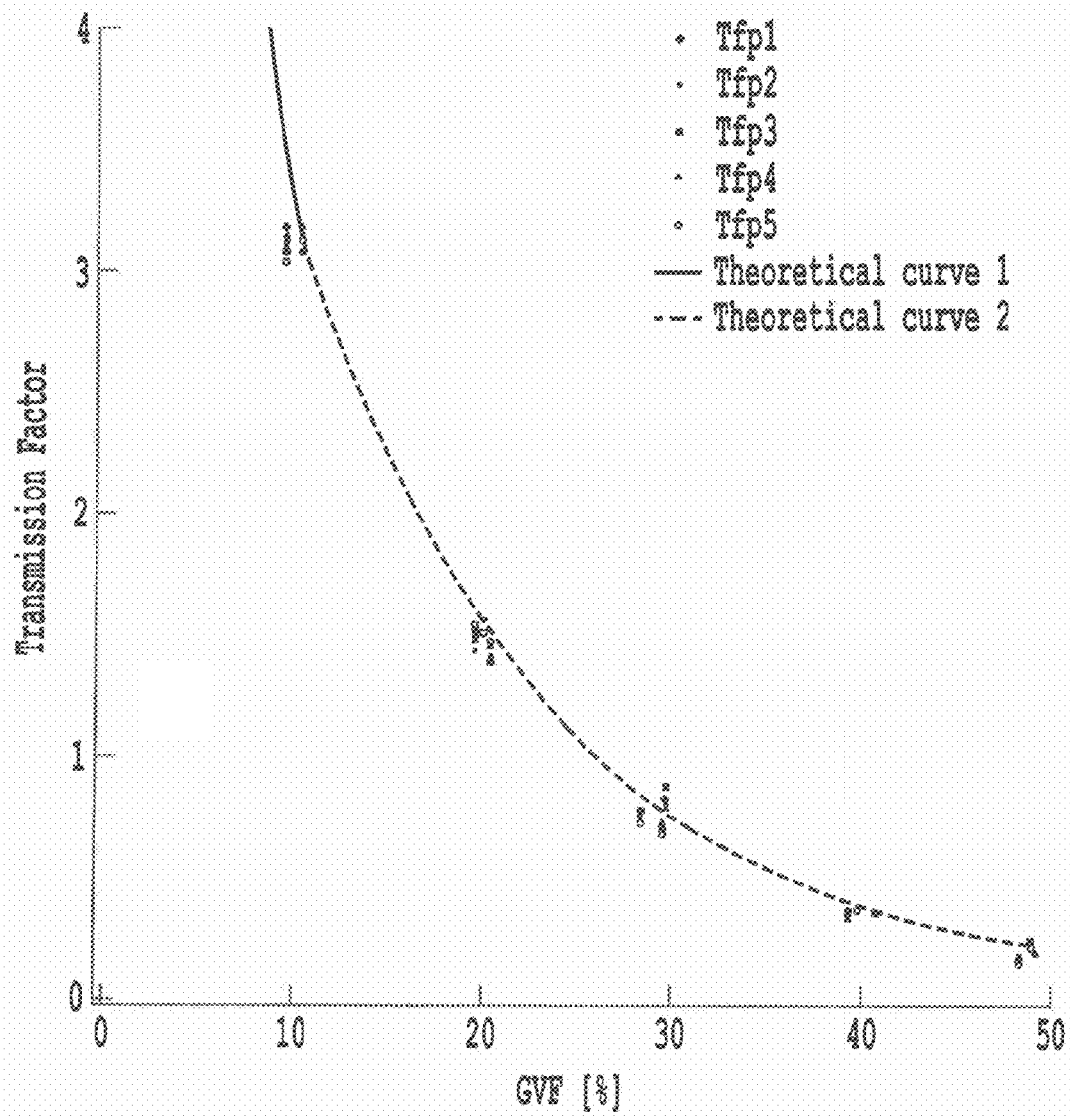
FIG. 16 is a graph showing pressure compensated experimental data for the ultrasound transmission factor versus gas volumetric fraction in the 10 to 50% range.
Figure 17:
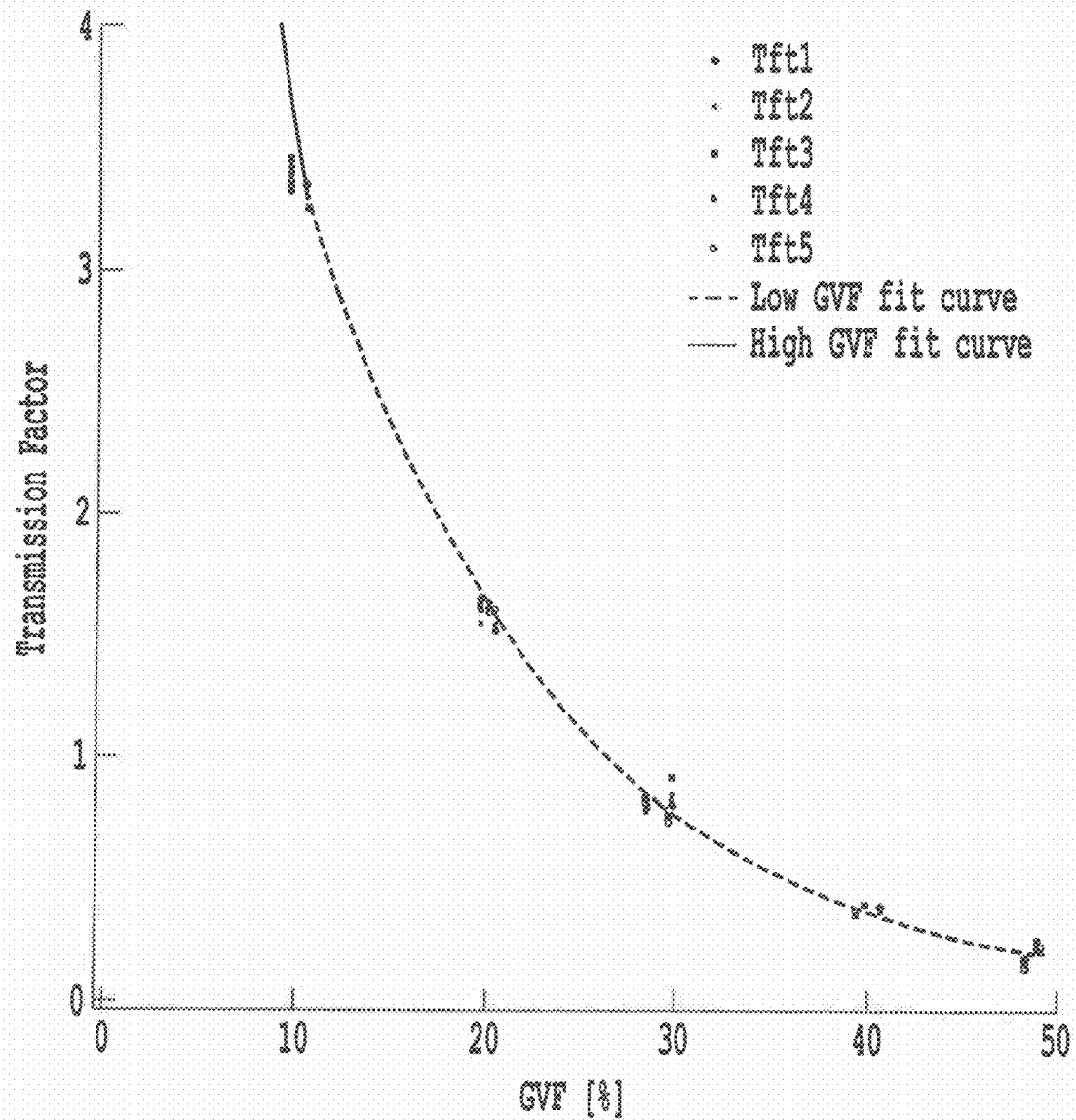
FIG. 17 is a graph showing pressure and temperature compensated experimental data for the ultrasound transmission factor versus gas volumetric fraction in the 10 to 50% range.

While there is a good agreement between the experimental data and the theoretical regression curves, the variations in the pressure and temperature between experiments could have a negative effect on the precision of the measurements. Since the pressure inside the pipe will influence the volume of the gas bubbles, but the back reflection of the ultrasound signal is dependent on the area of the bubbles, the dependence between the transmission factor and the pressure will be of the form, $$T_{fp0} = T_{fp} \left( \frac{P_0}{P_p} \right)^{\frac{2}{3}} \qquad \text{Eq. 7}$$

where $T_{fp0}$ is the transmission factor at a chosen standard pressure $P_0$, and $T_{fp}$ is the transmission factor obtained at the measured pressure $P_p$. Similarly, the temperature influence can be compensated by, $$T_{ft0} = T_{ft}\left(\frac{T_t}{T_0}\right)^{\frac{2}{3}} \quad \text{Eq. 8}$$

where $T_{ft0}$ is the transmission factor at a chosen standard temperature $T_0$, and $T_{ft}$ is the transmission factor obtained at the measured temperature $T_t$. Table 9 shows the ultrasound transmission factors corrected for a standard pressure $P_0=200$ psi and $T_0=40°$ C. The pressure compensated experimental data for the ultrasound transmission factor versus gas volumetric fraction in the 10 to 50% range are plotted in FIG. 16. FIG. 17 shows the experimental data compensated for both pressure and temperature. The statistical properties of the data set will be similar with those obtained for uncompensated data since the transformations involved only exact numbers.

TABLE 9

Pressure and temperature compensated experimental data for the ultrasound transmission factor versus gas volumetric fraction in the 10-50% range.

| Exp | GVF [%] | Water Cut [%] | Flow [lb/min] | Pressure [PSIg] | Temp [° C.] | Tft1 | Tft2 | Tft3 | Tft4 | Tft5 | Tftav |
|---|---|---|---|---|---|---|---|---|---|---|---|
| 1 | 0 | 25.76 | 861.36 | 196.9 | 43.3 | 21.184 | 20.831 | 21.558 | 21.293 | 20.942 | 21.162 |
| 2 | 10.32 | 26.68 | 842.245 | 193.92 | 43.26 | 3.353 | 3.296 | 3.257 | 3.363 | 3.315 | 3.317 |
| 3 | 19.89 | 27.13 | 839.787 | 193.98 | 43.39 | 1.618 | 1.651 | 1.639 | 1.603 | 1.589 | 1.620 |
| 4 | 29.60 | 27.31 | 856.554 | 194.05 | 43.46 | 0.854 | 0.866 | 0.928 | 0.840 | 0.816 | 0.861 |
| 5 | 39.66 | 27.04 | 873.406 | 189.67 | 43.94 | 0.395 | 0.410 | 0.392 | 0.380 | 0.384 | 0.392 |
| 6 | 48.86 | 27.05 | 834.26 | 178.51 | 44.65 | 0.219 | 0.239 | 0.257 | 0.241 | 0.228 | 0.237 |
| 7 | 9.495 | 22.58 | 1260.48 | 184.19 | 45.97 | 3.388 | 3.329 | 3.463 | 3.436 | 3.343 | 3.392 |
| 8 | 20.25 | 23.6 | 1261.54 | 184.84 | 46.01 | 1.559 | 1.545 | 1.521 | 1.593 | 1.613 | 1.566 |
| 9 | 29.45 | 24.15 | 1264.67 | 185.01 | 46.08 | 0.777 | 0.767 | 0.771 | 0.804 | 0.745 | 0.773 |
| 10 | 39.17 | 25.19 | 1256.81 | 175.37 | 46.28 | 0.354 | 0.372 | 0.385 | 0.356 | 0.378 | 0.369 |
| 11 | 48.26 | 26.26 | 1212.3 | 157.7 | 47.27 | 0.185 | 0.166 | 0.175 | 0.161 | 0.146 | 0.167 |

For the range 0 to 10% GVF the exponential regression:

$$T_{ft} = k_{L3} + k_{L4} e^{-k_{L5}GVF} \quad \text{Eq. 9}$$

where the regression coefficients values±one standard deviation were:
$k_{L3}=1.3765\pm0.0238$
$k_{L4}=19.785\pm0.0347$
$k_{L5}=0.22507\pm0.0019$ The regression was in excellent agreement with the data as shown by the extremely small $\chi^2=0.000653$.

For the 10 to 50% GVF range the regression equation, $$T_{ft} = k_{H3} + k_{H4} e^{-k_{H5}GVF} \quad \text{Eq. 10}$$

with $k_{H3}=0.014777\pm0.0415$
$k_{H4}=7.1369\pm0.2$
$k_{H5}=0.074839\pm0.00288$
and $\chi^2=0.00961833$.

The standard deviation of the regression coefficients improved by a factor of two and the value of $\chi^2$ reduced by an order of magnitude when compared with the values obtained for the uncompensated experimental data.

In order to obtain the gas volumetric fraction from the ultrasound transmission factor measurements, the expressions for the exponential regressions for GVF are solved. Thus, $$GVF = -\frac{1}{k_{L5}} \ln \frac{T_{ft} - k_{L3}}{k_{L4}} [\%], \quad \text{if } T_{ft} > 3.3 \quad \text{Eq. 11}$$

and, $$GVF = -\frac{1}{k_{H5}} \ln \frac{T_{ft} - k_{H3}}{k_{H4}} [\%], \quad \text{if } T_{ft} \leq 3.3 \quad \text{Eq. 12}$$

Figure 18:
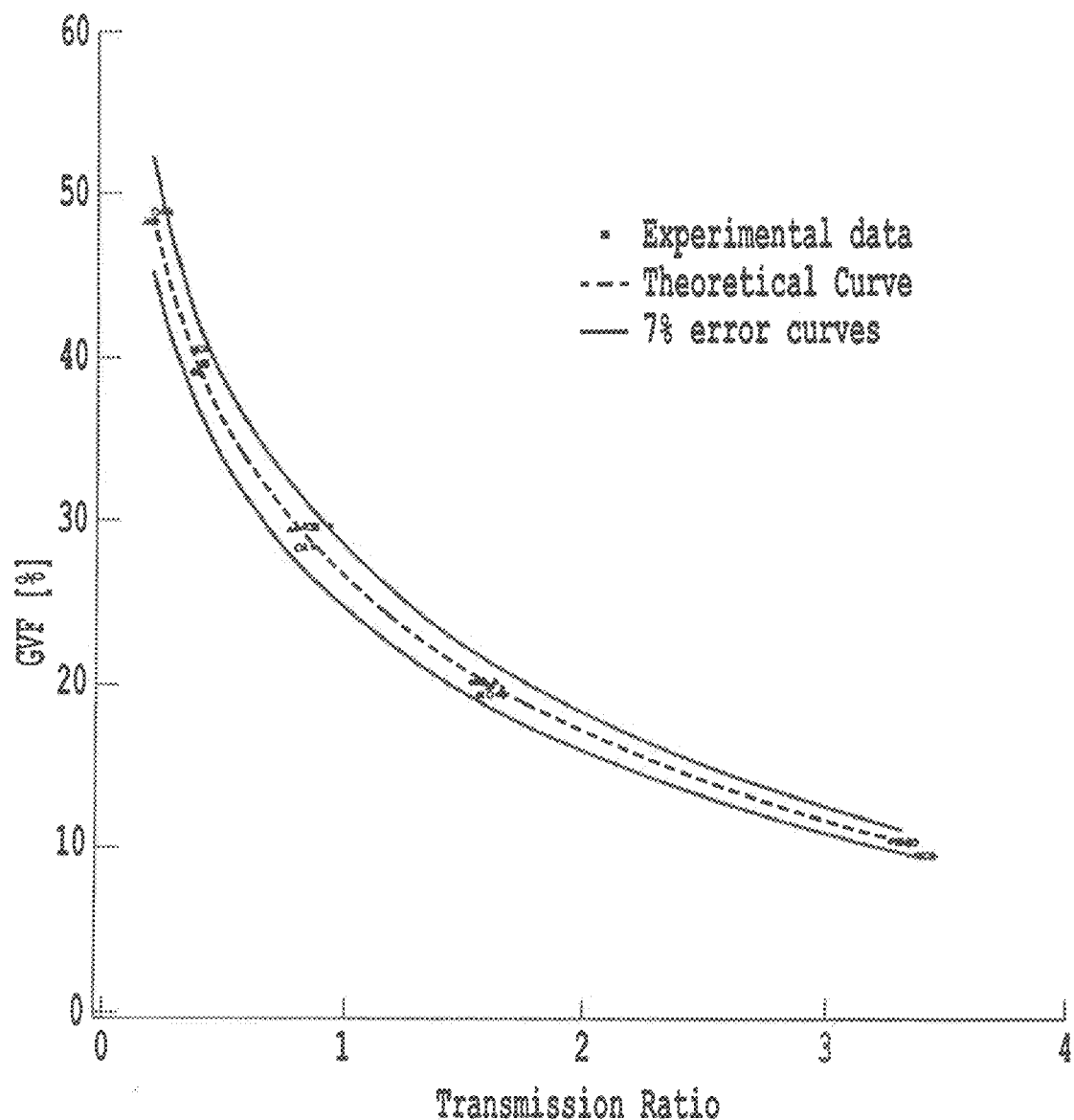
FIG. 18 is a graph showing gas volumetric fraction in the 10 to 50% range versus ultrasound transmission factor.

The results obtained using the multiphase flowmeter data were then compared with the corresponding values of the GVF obtained from the test loop instruments, and the percentage errors were calculated. As shown in Table 10 and FIG. 18, all errors are less than 7% with most of them around 2%. It should be noted that the value for the GVF provided by the test loop instruments represents a 3 minutes average. During this time the actual value of the GVF varied to a certain degree. The five measurements recorded with the research multiphase flowmeter represent 1 second snapshots of the GVF that captured the variability of the flow. Thus, the actual precision of the flowmeter is higher than the errors in Table 10 suggest. In actual use, averaging of the signals between measurements may produce much more precise results.

TABLE 10

Measured and experimental GVF for 25% water cut experiments.

| Exp | Experimental (loop) GVF [%] | Transmission factor | Measured GVF [%] | Error [%] |
|---|---|---|---|---|
| 1 | 0 | 21.162 | -1.72e-06 | -0.008 |
| 2 | 10.32 | 3.317 | 10.29 | 0.17 |
| 3 | 19.89 | 1.620 | 19.93 | -0.25 |
| 4 | 29.60 | 0.861 | 28.49 | 3.72 |
| 5 | 39.66 | 0.392 | 39.27 | 0.96 |
| 6 | 48.86 | 0.237 | 46.36 | 5.08 |
| 7 | 9.495 | 3.392 | 9.99 | -5.31 |
| 8 | 20.25 | 1.566 | 20.39 | -0.71 |
| 9 | 29.45 | 0.773 | 29.96 | -1.72 |
| 10 | 39.17 | 0.369 | 40.12 | -2.45 |
| 11 | 48.26 | 0.167 | 51.45 | -6.61 |

The robustness of the GVF measurements was tested in an additional set of 5 experiments using 50% water cut and GVF from 10 to 50%. The raw experimental data, and the pressure and temperature compensated ones, as well as the relevant statistical parameters are presented in Tables 11 to 15.

The results provided by the multiphase flowmeter were compared with the corresponding values obtained from the test loop instruments, and the percentage errors were calculated. As seen in Table 16 the errors were less than 6% as predicted.

TABLE 11

Experimental data for different gas volumetric fractions and 50% water cut.

| Exp | GVF [%] | Water Cut [%] | Flow [lb/min] | Pressure [PSIg] | Temp [° C.] | Trans. Volt. [V] | A1 | A2 | A3 | A4 | A5 |
|---|---|---|---|---|---|---|---|---|---|---|---|
| 12 | 9.46  | 49.93 | 888.457 | 189.46 | 45.02 | 30  | 236.425 | 232.479 | 228.173 | 233.735 | 230.481 |
| 13 | 19.44 | 50.71 | 877.162 | 189.88 | 45.28 | 50  | 188.385 | 176.928 | 185.275 | 182.342 | 191.417 |
| 14 | 28.31 | 51.44 | 884.183 | 189.96 | 45.72 | 70  | 125.624 | 127.751 | 134.285 | 129.378 | 130.723 |
| 15 | 40.55 | 51.34 | 885.573 | 182.65 | 46.21 | 90  | 74.291  | 78.541  | 75.482  | 76.552  | 78.499  |
| 16 | 49.04 | 53.16 | 873.349 | 172.21 | 46.77 | 100 | 46.249  | 48.527  | 44.150  | 41.372  | 48.441  |

TABLE 12

Error analysis for amplitude measurement for different gas volumetric fractions and 50% water cut.

| Exp | GVF [%] | Water Cut [%] | Flow [lb/min] | Pressure [PSIg] | Temp [° C.] | Trans. Volt. [V] | Aav | $\sigma_A$ | $\sigma_{Aav}$ | $\sigma_{Aav}$ % |
|---|---|---|---|---|---|---|---|---|---|---|
| 12 | 9.46  | 49.93 | 888.457 | 189.46 | 45.02 | 30  | 232.259 | 3.14 | 1.40 | 0.60 |
| 13 | 19.44 | 50.71 | 877.162 | 189.88 | 45.28 | 50  | 184.869 | 5.59 | 2.50 | 1.35 |
| 14 | 28.31 | 51.44 | 884.183 | 189.96 | 45.72 | 70  | 129.552 | 3.26 | 1.46 | 1.12 |
| 15 | 40.55 | 51.34 | 885.573 | 182.65 | 46.21 | 90  | 76.673  | 1.87 | 0.83 | 1.09 |
| 16 | 49.04 | 53.16 | 873.349 | 172.21 | 46.77 | 100 | 45.747  | 3.04 | 1.36 | 2.97 |

TABLE 13

Experimental data for ultrasound signal transmission factor at 50% water cut.

| Exp | GVF [%] | Water Cut [%] | Flow [lb/min] | Pressure [PSIg] | Temp [° C.] | Tf1 | Tf2 | Tf3 | Tf4 | Tf5 |
|---|---|---|---|---|---|---|---|---|---|---|
| 12 | 9.46  | 49.93 | 888.457 | 189.46 | 45.02 | 3.079 | 3.027 | 2.971 | 3.043 | 3.001 |
| 13 | 19.44 | 50.71 | 877.162 | 189.88 | 45.28 | 1.472 | 1.382 | 1.448 | 1.425 | 1.495 |
| 14 | 28.31 | 51.44 | 884.183 | 189.96 | 45.72 | 0.701 | 0.713 | 0.749 | 0.722 | 0.729 |
| 15 | 40.55 | 51.34 | 885.573 | 182.65 | 46.21 | 0.322 | 0.341 | 0.328 | 0.332 | 0.341 |
| 16 | 49.04 | 33.16 | 873.349 | 172.21 | 46.77 | 0.181 | 0.190 | 0.172 | 0.162 | 0.189 |

TABLE 14

Error analysis for ultrasound signal transmission factor at 50% water cut.

| Exp | GVF [%] | Water Cut [%] | Flow [lb/min] | Pressure [PSIg] | Temp [° C.] | Tfav | $\sigma_{Tf}$ | $\sigma_{Tfav}$ | $\sigma_{Tfav}$ % |
|---|---|---|---|---|---|---|---|---|---|
| 12 | 9.46  | 49.93 | 888.457 | 189.46 | 45.02 | 3.024 | 0.0409 | 0.0183 | 0.6047 |
| 13 | 19.44 | 50.71 | 877.162 | 189.88 | 45.28 | 1.444 | 0.0436 | 0.0195 | 1.3509 |
| 14 | 28.31 | 51.44 | 884.183 | 189.96 | 45.72 | 0.723 | 0.0182 | 0.0081 | 1.1248 |
| 15 | 40.55 | 51.34 | 885.573 | 182.65 | 46.21 | 0.333 | 0.0081 | 0.0036 | 1.0888 |
| 16 | 49.04 | 33.16 | 873.349 | 172.21 | 46.77 | 0.179 | 0.0119 | 0.0053 | 2.9702 |

TABLE 15

Pressure and temperature compensated experimental data for the ultrasound transmission factor versus gas volumetric fraction in the 10-50% range at 50% water cut.

| Exp | GVF [%] | Water Cut [%] | Flow [lb/min] | Pressure [PSIg] | Temp [° C.] | Tft1 | Tft2 | Tft3 | Tft4 | Tft5 | Tftav |
|---|---|---|---|---|---|---|---|---|---|---|---|
| 12 | 9.46  | 49.93 | 888.457 | 189.46 | 45.02 | 3.454 | 3.396 | 3.333 | 3.414 | 3.367 | 3.393 |
| 13 | 19.44 | 50.71 | 877.162 | 189.88 | 45.28 | 1.655 | 1.554 | 1.628 | 1.602 | 1.682 | 1.624 |
| 14 | 28.31 | 51.44 | 884.183 | 189.96 | 45.72 | 0.793 | 0.807 | 0.848 | 0.817 | 0.825 | 0.818 |
| 15 | 40.55 | 51.34 | 885.573 | 182.65 | 46.21 | 0.377 | 0.399 | 0.383 | 0.389 | 0.398 | 0.389 |
| 16 | 49.04 | 33.16 | 873.349 | 172.21 | 46.77 | 0.222 | 0.232 | 0.211 | 0.198 | 0.232 | 0.219 |

TABLE 16

Measured and experimental GVF for 50% water cut experiments.

| Exp | Experimental GVF [%] | Transmission factor | Measured GVF [%] | Error [%] |
|---|---|---|---|---|
| 12 | 9.46 | 3.39276 | 9.995 | −5.648 |
| 13 | 19.44 | 1.62405 | 19.9 | −2.358 |
| 14 | 28.31 | 0.817902 | 29.19 | −3.124 |
| 15 | 40.55 | 0.389222 | 39.39 | 2.881 |
| 16 | 49.04 | 0.219136 | 47.48 | 3.18 |

The percentage of oil in the oil/water/gas mixture is determined by subtracting the sum of the determined water and gas fractions from the total. Total flow may be determined in any suitable manner, for example, via a flow meter F1. Thus, the flow of oil (or non-water fluid) may be determined by subtraction as follows Flow Rate of Oil=Total Flow−Total Flow (water fraction+gas fraction)

Various modifications and variations of the present invention are possible in light of the above teachings. It is therefore to be understood that within the scope of the appended claims, the invention may be practiced otherwise than as specifically described herein. For example, while described in terms of both software and hardware components interactively cooperating, it is contemplated that the system described herein may be practiced entirely in software.

What is claimed:

1. A non-transitory computer readable medium containing program instructions for execution on a processor, which when executed by the processor, results in a performance of steps comprising:
    obtaining data relating to a pressure of a multiphase fluid in an interior of a main body;
    obtaining data relating to a temperature of the multiphase fluid;
    receiving data regarding an ultrasonic wave transmitted in the multiphase fluid wherein the data regarding the ultrasonic wave is obtained solely from one ultrasonic transducer-sensor pair of a plurality of ultrasonic transducer-sensor pairs; and
    determining a gas fraction, water fraction, and non-water fluid fraction of the multiphase fluid based on the data relating to the pressure of the multiphase fluid, the data relating to the temperature of the multiphase fluid, and the data regarding the ultrasonic wave transmitted in the multiphase fluid.

2. The non-transitory computer readable medium according to claim 1, further containing program instructions for execution on the processor, which when executed by the processor, results in a performance of steps comprising:
    obtaining data relating to a flow rate of the multiphase fluid flowing in the interior of the main body; and
    sending to the processor a signal that includes the data relating to the flow rate of the multiphase fluid.

3. The non-transitory computer readable medium according to claim 2, further containing program instructions for execution on the processor, which when executed by the processor, results in a performance of steps comprising:
    determining a flow rate of a non-water liquid flowing in the interior of the main body based on the determined gas fraction, water fraction, and the measured flow rate of the multiphase fluid flowing in the interior of the main body.

4. The non-transitory computer readable medium according to claim 1, further containing program instructions for execution on the processor, which when executed by the processor, results in a performance of steps comprising:
    determining a velocity of the ultrasonic wave based on a detection performed by an ultrasonic sensor; and
    determining the water fraction of the multiphase fluid based on the determined velocity of the ultrasonic wave.

5. The non-transitory computer readable medium according to claim 4, further containing program instructions for execution on the processor, which when executed by the processor, results in a performance of steps comprising:
    adjusting the determined velocity of the ultrasonic wave to compensate for a difference between a temperature sensed by a temperature sensor and a standard temperature and to compensate for a difference between a pressure sensed by a pressure sensor and a standard pressure.

6. The non-transitory computer readable medium according to claim 5, further containing program instructions for execution on the processor, which when executed by the processor, results in a performance of steps comprising:
    adjusting the determined velocity of the ultrasonic wave with the relationship:

$$V_w = k_0 + k_1 T + k_2 T^2 + k_3 T^3 + k_4 T^4 + k_5 T^5 + k_p P$$

where $V_w$ is the adjusted velocity of the ultrasonic wave, T is the temperature of the multiphase fluid sensed by the temperature sensor, and P is the pressure of the multiphase fluid sensed by the pressure sensor, and $k_o$, $k_1$, $k_2$, $k_3$, $k_4$, $k_5$, and $k_p$ are constants having appropriate dimensions.

7. The non-transitory computer readable medium according to claim 4, further containing program instructions for execution on the processor, which when executed by the processor, results in a performance of steps comprising:
    determining the water fraction we in the multiphase fluid based on a water fraction determination equation:

$$wc = \frac{-k_1 + \sqrt{k_1^2 - 4k_2(k_0 + V_w)}}{2k_2}$$

where $k_o$, $k_1$, and $k_2$ are constants having appropriate dimensions, and $V_w$ is the determined velocity of the ultrasonic wave.

8. The apparatus according to claim 7, wherein, when numerical values are substituted for $k_o$, $k_1$, and $k_2$ and $k_o$, $k_1$, and $k_2$ have appropriate dimensions, the water fraction determination equation is:

$$wc = 55.9159\sqrt{0.035768 V_w - 45.3369} - 64.0405.$$

9. The non-transitory computer readable medium according to claim 4, further containing program instructions for execution on the processor, which when executed by the processor, results in a performance of steps comprising:
    determining the gas fraction in the multiphase fluid based on a transmission factor corresponding to attenuation of the ultrasonic wave transmitted by the ultrasonic transducer and detected by the ultrasonic sensor.

10. The non-transitory computer readable medium according to claim 9, further containing program instructions for execution on the processor, which when executed by the processor, results in a performance of steps comprising:
    determining the gas fraction GVF in the multiphase fluid by the equation:

$$GVF = -\frac{1}{k_{H5}} \ln \frac{T_{ft} - k_{H3}}{k_{H4}}$$

where $T_{ft}$ is a transmission factor proportional to the attenuation of the ultrasound wave and $k_{H3}$, $k_{H4}$, and $k_{H5}$ are constants having appropriate dimensions.

11. The non-transitory computer readable medium according to claim 9, further containing program instructions for execution on the processor, which when executed by the processor, results in a performance of steps comprising:

Adjusting the transmission factor $T_{ft}$ to compensate for a difference between a fluid temperature sensed by the temperature sensor and a standard temperature and to compensate for a difference between a fluid pressure sensed by the pressure sensor and a standard pressure.

12. The non-transitory computer readable medium according to claim 9, further containing program instructions for execution on the processor, which when executed by the processor, results in a performance of steps comprising:

applying a first equation to determine the gas fraction in the multiphase fluid when the gas fraction in the multiphase fluid is below 10% and a second equation when the gas fraction in the multiphase fluid when the gas fraction in the multiphase fluid is equal to or above 10%.

13. A non-transitory computer readable medium containing program instructions for execution on a processor, which when executed by the processor, results in a performance of steps that comprise a method of determining fractions of various phases in a multiphase fluid, the method comprising the steps of:

sensing a pressure of the multiphase fluid;
sensing a temperature of the multiphase fluid;
transmitting and detecting an ultrasonic wave in the multiphase fluid a single ultrasonic transducer-sensor pair of a plurality of ultrasonic transducer-sensor pairs;
determining a gas fraction, water fraction, and non-water fluid fraction of the multiphase fluid based on the sensed pressure, sensed temperature, and at least one characteristic of the ultrasonic wave detected by the single ultrasonic transducer-sensor pair of the plurality of ultrasonic transducer-sensor pairs.

14. The non-transitory computer readable medium according to claim 13 further containing program instructions for execution on the processor, which when executed by the processor, results in a performance of steps comprising:

measuring a flow rate of the multiphase fluid; and
determining a flow rate of the non-water fluid based on the determined gas fraction, water fraction, and measured flow rate of the multiphase fluid.

15. The non-transitory computer readable medium according to claim 13, further containing program instructions for execution on the processor, which when executed by the processor, results in a performance of steps wherein the step of determining a gas fraction, water fraction, and non-water fluid fraction comprises:

determining a velocity of the detected ultrasonic wave transmitted in the multiphase fluid and determining a water fraction based on the determined velocity.

16. The non-transitory computer readable medium according to claim 15 further containing program instructions for execution on the processor, which when executed by the processor, results in a performance of steps comprising:

adjusting the determined velocity of the detected ultrasonic wave to compensate for a difference between a sensed temperature of the multiphase fluid and a standard temperature and to compensate for a difference between a sensed pressure of the multiphase fluid and a standard pressure.

17. The non-transitory computer readable medium according to claim 16, further containing program instructions for execution on the processor, which when executed by the processor, results in a performance of steps comprising:

adjusting the determined velocity includes applying the equation:

$$V_w = k_0 + k_1 T + k_2 T^2 + k_3 T^{3+} k_4 T^{4+} k_5 T^6 + p_p P$$

to determine an adjusted velocity $V_w$, where T is a sensed temperature of the multiphase fluid, and P is a sensed pressure of the multiphase fluid, and $k_0$, $k_1$, $k_2$, $k_3$, $k_4$, $k_5$, and $k_p$ are constants having appropriate dimensions.

18. The non-transitory computer readable medium according to claim 15, further containing program instructions for execution on the processor, which when executed by the processor, results in a performance of steps comprising:

determining the water fraction using the following water fraction determination equation:

$$wc = \frac{-k_1 + \sqrt{k_1^2 - 4k_2(k_0 + V_w)}}{2k_2}$$

where wc is the water faction, $k_o$, $k_1$, and $k_2$ are constants having appropriate dimensions, and $V_w$ is the determined velocity of the ultrasonic wave.

19. The non-transitory computer readable medium according to claim 18, further containing program instructions for execution on the processor, which when executed by the processor, results in a performance of steps wherein, when numerical values are substituted for $k_o$, $k_1$, and $k_2$ and $k_0$, $k_1$, and $k_2$ have appropriate dimensions, the water fraction determination equation is:

$$wc = 55.9159\sqrt{0.035768 V_w - 45.3369} - 64.0405.$$

20. The non-transitory computer readable medium according to claim 15, further containing program instructions for execution on the processor, which when executed by the processor, results in a performance of steps comprising:

determining the gas fraction in the multiphase fluid based on a transmission factor corresponding to attenuation of the ultrasonic wave between the transmitting and detecting of the ultrasonic wave.

21. The non-transitory computer readable medium according to claim 15, further containing program instructions for execution on the processor, which when executed by the processor, results in a performance of steps wherein the step of determining the gas fraction is performed via the equation:

$$GVF = -\frac{1}{k_{H5}} \ln \frac{T_{ft} - k_{H3}}{k_{H4}}$$

wherein GVF is the gas fraction, $T_{ft}$ is a transmission factor directly proportional to the attenuation of the ultrasound wave and $k_{H3}$, $k_{H4}$, and $k_{H5}$ are constants having appropriate dimensions.

22. The non-transitory computer readable medium according to claim 21, further containing program instructions for execution on the processor, which when executed by the processor, results in a performance of steps comprising:

Adjusting the transmission factor $T_{ft}$ to compensate for a difference between a sensed temperature of the multiphase fluid and a standard temperature and to compensate for a difference between a sensed pressure of the multiphase fluid and a standard pressure.

23. The non-transitory computer readable medium according to claim 22, further containing program instructions for execution on the processor, which when executed by the processor, results in a performance of steps comprising:

applying a first equation to determine the gas fraction when the gas fraction is below 10% and applying a second equation to determine the gas fraction when the gas fraction is equal to or above 10%.

* * * * *